United States Patent
MacMillan et al.

(10) Patent No.: US 6,900,357 B2
(45) Date of Patent: May 31, 2005

(54) DIRECT, ENANTIOSELECTIVE ALDOL COUPLING OF ALDEHYDES USING CHIRAL ORGANIC CATALYSTS

(75) Inventors: David W. C. MacMillan, Pasadena, CA (US); Alan B. Northrup, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/420,339

(22) Filed: Apr. 21, 2003

(65) Prior Publication Data

US 2004/0024221 A1 Feb. 5, 2004

Related U.S. Application Data

(60) Provisional application No. 60/376,878, filed on May 1, 2002, and provisional application No. 60/373,871, filed on Apr. 19, 2002.

(51) Int. Cl.[7] .............................................. C07C 45/72
(52) U.S. Cl. ...................................... 568/458; 568/463
(58) Field of Search .................................. 568/458, 463

(56) References Cited

U.S. PATENT DOCUMENTS

| | | | |
|---|---|---|---|
| 4,324,884 A | 4/1982 | White et al. | ................. 528/207 |
| 4,355,184 A | 10/1982 | Kaku et al. | .................... 568/31 |
| 4,528,405 A | 7/1985 | Papa | .......................... 568/463 |

(Continued)

FOREIGN PATENT DOCUMENTS

| | | |
|---|---|---|
| WO | WO 92/02505 | 2/1992 |
| WO | WO 03/047740 | 6/2003 |

OTHER PUBLICATIONS

Ahrendt et al. (2000), "New Strategies for Organic Catalysis: The First Highly Enantioselective Organocatalytic Diels—Alder Reaction," *J. Am. Chem. Soc.* 122(17):4243–4244.
Evans et al. (1997), "Chiral C$_2$-Symmetric Cu(II) Complexes as Catalysts for Enantioselective Intramolecular Diels–Alder Reactions. Asymmetric Synthesis of (–)-Isopulo'upone," *J. Org. Chem.* 62(4):786–787.
Frederickson (1997), "Opitcally Active Isoxazolidines via Asymmetric Cycloaddition Reactions of Nitrones with Alkenes: Applications in Organic Synthesis," *Tetrahedron* 53(2):403–425.
Ishihara et al. (1996), "A New Powerful and Practical BLA Catalyst for Highly Enantioselective Diels–Alder Reations: An Extreme Acceleration of Reaction Rate by Brønsted Acid," *J. Am. Chem. Soc.* 118(12):3049–3050.
Iwasawa et al. (1989), "Asymmetric Intramolecular Diels–Alder Reaction Catalyzed by the Chiral Titanium Reagent," *Chemistry Letters*, pp. 1947–1950.
Jen et al. (2000), "New Strategies for Organic Catalysis: The First Enantioselective Organocatalytic 1,3–Dipolar Cycloaddition," *J. Am. Chem. Soc.* 122(40):9874–9875.
Jensen et al. (2001), "Catalytic Asymmetric Friedel–Crafts Alkylation of β,γ–Unsaturated α–Ketoesters: Enantioselective Addition of Aromatic C–H Bonds to Alkenes," *Angew. Chem. Int. Edit.* 40(1):160–163.
Johannsen (1999), "An Enantioselective Synthesis of Heteroaromatic N–Tosyl α–Amino Acids," *Chem. Commun.*, pp. 2233–2234.
Maruoka et al. (1994), "Virtually Complete Blocking of α,β–Unsaturated Aldehyde Carbonyls by Complexation with Aluminum Tris(2,6–diphenylphenoxide)," *J. Am. Chem. Soc.* 116(9):4131–4132.
Northrup et al. (2002), "The First Direct and Enantioselective Cross–Aldol Reaction of Aldehydes," J. Am. Chem. Soc. Supporting Information, Northrup ja0262378, pp. S1–S7.
Ohta et al. (1996), "Novel 5–Hydroxytryptamine (5–HT$_3$) Receptor Antagonists. III. Pharamcological Evaluations and Molecular Modeling Studies of Optically Active 4,5,6, 7–Tetrahydro–1H–Benzimidazole Derivatives," *Chem. Pharm. Bull.* 44(9):1707–1716.
Paras et al. (2001), "New Strategies in Organic Catalysis: The First Enantioselective Organocatalytic Friedel–Crafts Alkylation," *J. Am. Chem. Soc.* 123(18):4370–4371.
Schuster et al. (2000), "Catalysis of a Diels—Alder Reaction by Amidinium Ions," J. Org. Chem. 65:1697–1701.
Shi et al. (1995), "Synthesis of Axially Dissymmetric Chiral Ammonium Salts by Quaternization of Secondary Amines with (R)–(+)–2,2'–Bis(bromomethyl)–6,6'–dinitrobiphenyl and (R)–(+)–2,2'–Bis(bromomethyl)–1,1'–binaphthyl and an Examination of Their Abilities as Chiral Phase–Transfer Catalysts," *J. Chem. Research (S)*, pp. 46–47 (*J. Chem. Research (M)*, pp. 0401–0411).
Solodin et al. (1990), "(5S)–5–Benzyl–2,2,3–trimethylimidazolidin–4–one as a Highly Effective Chiral Auxiliary for Asymmetric Reduction of α–Oxo Amides," *J. Chem. Soc., Chem. Commun.*, pp. 1321–1322.
Yang et al. (1998), "Design and Synthesis of Chiral Ketones for Catalytic Asymmetric Epoxidation of Unfunctionalized Olefins," *J. Am. Chem. Soc.* 120(24):5943–5952.

U.S. PATENT DOCUMENTS

*Primary Examiner*—Johann Richter
*Assistant Examiner*—Sikarl A. Witherspoon
(74) *Attorney, Agent, or Firm*—Dianne E. Reed; Reed Intellectual Property Law Group

(57) ABSTRACT

Nonmetallic, chiral organic catalysts are used to catalyze an enantioselective aldol coupling reaction between aldehyde substrates. The reaction may be carried out with a single enolizable aldehyde, resulting in dimerization to give a β-hydroxy aldehyde, or trimerization to give a dihydroxy tetrahydropyran. The reaction may also conducted with an enolizable aldehyde and a second aldehyde, which may or may not be enolizable, so that the coupling is a cross-aldol reaction in which the α-carbon of the enolizable aldehyde adds to the carbonyl carbon of the second aldehyde in an enantioselective fashion. Reaction systems composed of at least one enolizable aldehyde, an optional additional aldehyde, and the nonmetallic chiral organic catalyst are also provided, as are methods of implementing the enantioselective aldol reaction in the synthesis of sugars.

66 Claims, No Drawings

U.S. PATENT DOCUMENTS

| | | |
|---|---|---|
| 5,428,174 A | 6/1995 | Reissenweber et al. ..... 548/247 |
| 5,430,194 A | 7/1995 | Barner et al. ............... 568/429 |
| 5,786,373 A | 7/1998 | Hartman et al. ............ 514/326 |
| 5,977,290 A | 11/1999 | Siebenhaar .................. 528/239 |
| 6,040,262 A | 3/2000 | Fougret et al. ............. 502/162 |
| 6,307,057 B1 | 10/2001 | MacMillan et al. ...... 548/316.4 |
| 6,369,243 B1 | 4/2002 | MacMillan et al. ......... 549/459 |

DIRECT, ENANTIOSELECTIVE ALDOL COUPLING OF ALDEHYDES USING CHIRAL ORGANIC CATALYSTS

CROSS-REFERENCE TO RELATED APPLICATIONS

This application claims priority under 35 U.S.C. §119(e)(1) to provisional U.S. Patent Applications Ser. No. 60/373,871, filed Apr. 19, 2002, and No. 60/376,878, filed May 1, 2002. The disclosures of the aforementioned applications are incorporated by reference in their entireties.

TECHNICAL FIELD

This invention relates generally to catalysis of enantioselective reactions, and more particularly relates to enantioselective reactions involving the use of chiral organic compounds to catalyze the direct coupling of aldehydes via an aldol reaction. The invention has utility in the fields of catalysis and organic synthesis, including organocatalysis and chiral chemistry.

BACKGROUND

The aldol reaction is one of the fundamental synthetic routes used by organic chemists to form new carbon-carbon bonds. The reaction involves the addition of a first aldehyde or ketone, as a nucleophile, to a second aldehyde or ketone that acts as an electrophile. Mechanistically, the α-carbon atom of the first aldehyde or ketone adds to the carbonyl carbon of the second aldehyde or ketone. The product is a β-hydroxy aldehyde (i.e., an "aldol") or ketone, which may serve as an intermediate in the context of a more complex reaction, or may represent the final product. Conventionally, aldol reactions involve a preliminary step in which the first aldehyde or ketone is converted to a nucleophile by forming the corresponding enolate, using a base, or the corresponding enol, using an acid.

Over the last three decades, seminal research has established the aldol reaction as the principal chemical reaction for the stereoselective construction of complex polyol architecture. Evans et al. (1979) J. Am. Chem. Soc. 101:6120; Evans et al. (1981) J. Am. Chem. Soc. 103:2127; Heathcock, C. H. Asymmetric Synthesis; Morrion, J. D., Ed.; Academic Press: New York, 1984; Vol. 3, part B, p 111; Danda et al. (1980) J. Org. Chem. 55:173; Masamune et al. (1981) J. Am. Chem. Soc. 103:1566; Masamune et al. (1986) J. Am. Chem. Soc. 108:8279; Mukaiyama, "The Directed Aldol Reaction," in Organic Reactions, New York, 1982; Vol. 28, p 203; Kobayashi et al. (1993) Tetrahedron 49:1761. More recently, several researchers have described attempts to achieve enantioselective "direct" aldol reactions, i.e., aldol reactions that do not require the pregeneration of enolates or enolate equivalents. See, e.g., List et al. (2000) J. Am. Chem. Soc. 122:2395; Notz et al. (2000) J. Am. Chem. Soc. 122:7386; Trost et al. (2000) J. Am. Chem. Soc. 122:12003; Yamada et al. (1997) Angew. Chem. Int. Ed. Engl. 36:1871; Yoshikawa et al. (1999) J. Am. Chem. Soc. 121:4168. These efforts have given rise to a new goal, the development of catalytic methods that allow the direct coupling of aldehyde substrates, illustrated in Scheme 1:

SCHEME 1

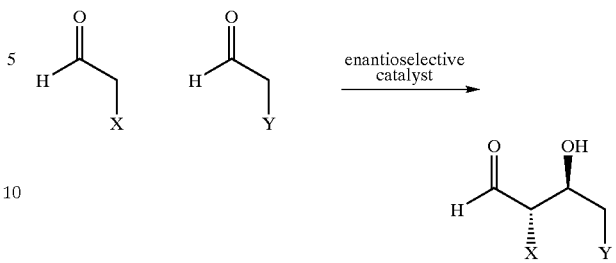

To date, direct, enantioselective coupling of aldehyde substrates has been achieved only with enzymatic catalysis (see Gijsen et al. (1994) J. Am. Chem. Soc. 116:8422). In addition, the enantioselective aldol coupling of non-equivalent aldehydes has been viewed as a particularly formidable synthetic challenge, because of (i) the propensity of aldehydes to polymerize under metal-catalyzed conditions and (ii) the mechanistic requirement that non-equivalent aldehydes must selectively partition into two discrete components, a nucleophilic donor and an electrophilic acceptor. Accordingly, an efficient and operationally simple method for carrying out direct, enantioselective coupling of aldehydes, including non-equivalent aldehydes, would be an enormously powerful tool in the field of synthetic organic chemistry. The present invention now provides such a method using chiral organic catalysts.

Many catalysts of organic reactions, including aldol coupling reactions, are organometallic complexes. Unfortunately, many organometallic reagents are expensive, and, depending on their catalytic activity, they may not be commercially viable. Moreover, many organometallic complexes are useful in conjunction with very specific reactants and reactions, a problem that is exacerbated in the catalysis of reactions leading to chiral molecules, particularly the conversion of either chiral or achiral molecules via enantioselective catalysis to provide a chiral product. Despite the observed need, relatively few asymmetric transformations have been reported that employ organic molecules as reaction catalysts. Recently, as described in U.S. Pat. No. 6,307,057 to MacMillan and U.S. Pat. No. 6,369,243 to MacMillan et al., certain organic catalysts have been synthesized that facilitate enantioselective transformations by lowering the LUMO (lowest unoccupied molecular orbital) of a reactant such as an α,β-unsaturated carbonyl compound to facilitate reaction thereof. The organic catalysts are acid addition salts of nonmetallic compounds containing a Group 15 or Group 16 heteroatom, e.g., salts of chiral amines, exemplified by the imidazolidinone salt (5S)-5-benzyl-2,2,3-trimethylimidazolidin-4-one hydrochloride.

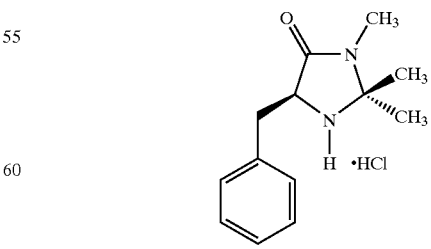

It has now been quite unexpectedly discovered that certain imidazolidinones and other chiral organic compounds, including, without limitation, those described in the '057 and '243 patents, are useful in catalyzing aldol coupling reactions of aldehydes in an enantioselective fashion. The invention represents a significant advance in the field of synthetic organic chemistry, insofar as the present methodology enables not only enantioselective aldol reactions of aldehydes, but also direct, enantioselective aldol coupling reactions using aldehydes as both aldol donor and aldol acceptor. The method provides for the enantioselective access to β-hydroxy aldehydes—important synthons in polypropionate and polyacetate natural product synthesis—as well as hydroxyvinyl polymers and oxygen heterocycles, including naturally occurring and synthetic sugars.

SUMMARY OF THE INVENTION

Accordingly, the invention provides a method for carrying out an aldol reaction using aldehydes as both aldol donor and the aldol acceptor, i.e., as the nucleophilic and electrophilic reactants, respectively. The reaction is carried out catalytically, using a nonmetallic, organic compound as the catalyst. The catalysts are readily synthesized from inexpensive, commercially available reagents, compatible with aerobic conditions, and provide the desired aldol coupling products in excellent yields with a high level of enantioselectivity.

In a first aspect of the invention, then, a method is provided for carrying out an enantioselective aldol coupling reaction between aldehyde molecules, comprising contacting (a) an enolizable aldehyde and optionally (b) an additional aldehyde, with (c) a catalytically effective amount of a nonmetallic chiral catalyst containing a Group 15 or Group 16 heteroatom. Any enolizable aldehyde may be employed, meaning that the aldehyde may be substituted with any nonhydrogen substituent (provided that the substituent not interfere with the aldol coupling reaction), so long as the α-carbon of the aldehyde contains a single enolizable hydrogen atom. With a single enolizable aldehyde, the reaction will proceed as a dimerization or trimerization reaction, resulting in a β-hydroxy aldehyde or a dihydroxy tetrahydropyran. Such reactions are illustrated below:

SCHEME 2

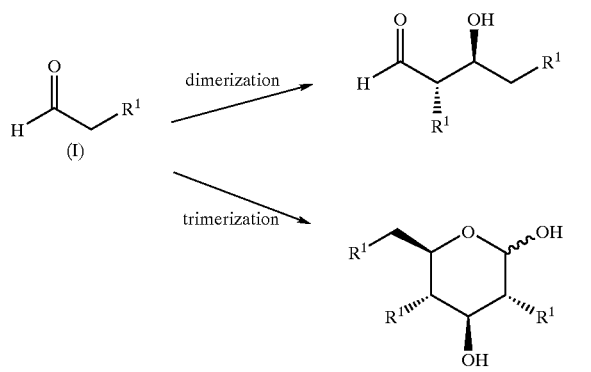

$R^1$ is selected from hydrocarbyl, substituted hydrocarbyl, heteroatom-containing hydrocarbyl, substituted heteroatom-containing hydrocarbyl, and functional groups. Preferred catalysts are cyclic secondary amines, exemplified by L-proline, (2S,5S)-5-benzyl-2-tert-butyl-3-methylimidazolidin-4-one, and salts and analogs thereof. When two or more aldehyde reactants are employed, the reaction proceeds as a "cross-aldol" reaction in which the α-carbon of an enolizable aldehyde undergoes nucleophilic addition to the carbonyl carbon of an additional aldehyde.

The second aldehyde may or may not be enolizable, and is generally represented by formula (II)

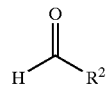

(II)

in which $R^2$ is defined as for $R^1$.

The reaction product(s) of the present aldol coupling reactions may be isolated, purified, and subject to further reaction, wherein, for example, a hydroxyl group is protected, derivatized as an ether, ester, or the like, or used as a nucleophile in a reaction with an electrophilic co-reactant, or a carbonyl group is reduced to a hydroxyl group or modified via a further nucleophilic addition reaction, e.g., in a further aldol reaction with an additional carbonyl-containing compound. Alternatively, further reaction may be carried out in the context of a "one-pot" synthesis, in which case the initial product of the aldol reaction is not isolated prior to subsequent modification.

The method of the invention may be implemented in the enantioselective, organocatalyzed synthesis of sugar molecules, when an enolizable aldehyde bearing a protected α-hydroxy group is used as a substrate. Such a substrate is generally of formula (I) wherein $R^1$ is —O—Pr in which Pr is a hydroxyl-protecting group. In most cases, it is desirable that the aldol coupling reaction proceed so as to result in trimerization of at least one enolizable aldehyde to give a protected dihydroxy tetrahydropyran. Alternatively, the aldol coupling reaction can result in dimerization of at least one enolizable aldehyde, and the dimer so provided is then further reacted, e.g., in an additional aldol reaction, to give a protected dihydroxy tetrahydropyran. In a preferred sugar synthesis, two enolizable aldehydes each α-substituted with a protected hydroxyl group are used as substrates, wherein the protected hydroxyl group of the first enolizable aldehyde is of the formula —O—$Pr^1$ and the protected hydroxyl group of the second enolizable aldehyde is of the formula —O—$Pr^2$, and $Pr^1$ and $Pr^2$ are different, preferably orthogonally removable under conditions generally used in carbohydrate synthesis.

In another embodiment, a reaction system is provided that comprises a nonmetallic chiral catalyst containing a Group 15 or Group 16 heteroatom, an enolizable aldehyde having the structure of formula (I) and, optionally, an additional aldehyde has the structure of formula (II)

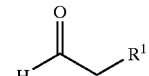

(I)

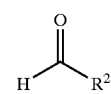

(II)

in which $R^1$ and $R^2$ are defined above.

DETAILED DESCRIPTION OF THE PREFERRED EMBODIMENTS

Unless otherwise indicated, the invention is not limited to specific molecular structures, substituents, synthetic methods, reaction conditions, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a catalyst" includes a single catalyst as well as a combination or mixture of two or more catalysts, reference to "a substituent" encompasses a single substituent as well as two or more substituents, and the like.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a chloro, bromo, fluoro or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$–$C_{24}$ alkoxy, $C_2$–$C_{24}$ alkenyloxy, $C_2$–$C_{24}$ alkynyloxy, $C_5$–$C_{24}$ aryloxy, $C_6$–$C_{24}$ aralkyloxy, $C_6$–$C_{24}$ alkaryloxy, acyl (including $C_2$–$C_{24}$ alkylcarbonyl (—CO-alkyl) and $C_6$–$C_{24}$ arylcarbonyl (—CO-aryl)), acyloxy (—O-acyl, including $C_2$–$C_{24}$ alkylcarbonyloxy (—O—CO-alkyl) and $C_6$–$C_{24}$ arylcarbonyloxy (—O—CO-aryl)), $C_2$–$C_{24}$ alkoxycarbonyl (—(CO)—O-alkyl), $C_6$–$C_{24}$ aryloxycarbonyl (—(CO)—O-aryl), halocarbonyl (—CO)—X where X is halo), $C_2$–$C_{24}$ alkylcarbonato (—O—(CO)—O-alkyl), $C_6$–$C_{24}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH ($C_1$–$C_{24}$ alkyl)), di-($C_1$-$C_{24}$ alkyl)-substituted carbamoyl (—(CO)—N($C_1$–$C_{24}$ alkyl)$_2$), mono-($C_5$–$C_{24}$ aryl)-substituted carbamoyl (—(CO)—NH-aryl), di-($C_5$–$C_{24}$ aryl)-substituted carbamoyl (—(CO)—N ($C_5$–$C_{24}$ aryl)$_2$), di-N-($C_1$–$C_{24}$ alkyl),N-($C_5$–$C_{24}$ aryl)-substituted carbamoyl, thiocarbamoyl (—(CS)—NH$_2$), mono-($C_1$–$C_{24}$ alkyl)-substituted thiocarbamoyl (—(CO)—NH($C_1$–$C_{24}$ alkyl)), di-($C_1$–$C_{24}$ alkyl)-substituted thiocarbamoyl (—(CO)—N($C_1$–$C_{24}$ alkyl)$_2$), mono-($C_5$–$C_{24}$ aryl)-substituted thiocarbamoyl (—(CO)—NH-aryl), di-($C_5$–$C_{24}$ aryl)-substituted thiocarbamoyl (—(CO)—N($C_5$–$C_{24}$ aryl)$_2$), di-N-($C_1$–$C_{24}$ alkyl),N-($C_5$–$C_{24}$ aryl)-substituted thiocarbamoyl, carbamido (—NH—(CO)—NH$_2$), cyano(—C≡N), cyanato (—O—C≡N), thiocyanato (—S—CN), formyl (—(CO)—H), thioformyl (—(CS)—H), amino (—NH$_2$), mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, $C_2$–$C_{24}$ alkylamido (—NH—(CO)-alkyl), $C_6$–$C_{24}$ arylamido (—NH—(CO)-aryl), imino (—CR=NH where R=hydrogen, $C_1$–$C_{24}$ alkyl, $C_5$–$C_{24}$ aryl, $C_6$–$C_{24}$ alkaryl, $C_6$–$C_{24}$ aralkyl, etc.), $C_2$–$C_{20}$ alkylimino (—CR=N(alkyl), where R=hydrogen, $C_1$–$C_{24}$ alkyl, $C_5$–$C_{24}$ aryl, $C_6$–$C_{24}$ alkaryl, $C_6$–$C_{24}$ aralkyl, etc.), arylimino (—CR=N(aryl), where R=hydrogen, $C_1$–$C_{20}$ alkyl, $C_5$–$C_{24}$ aryl, $C_6$–$C_{24}$ alkaryl, $C_6$–$C_{24}$ aralkyl, etc.), nitro (—NO$_2$), nitroso (—NO), sulfo (—SO$_2$—OH), sulfonato (—SO$_2$—O⁻), $C_1$–$C_{24}$ alkylsulfanyl (—S-alkyl; also termed "alkylthio"), $C_5$–$C_{24}$ arylsulfanyl (—S-aryl; also termed "arylthio"), $C_1$–$C_{24}$ alkylsulfinyl (—(SO)-alkyl), $C_5$–$C_{24}$arylsulfinyl (—(SO)-aryl), $C_1$–$C_{24}$ alkylsulfonyl (—SO$_2$-alkyl), $C_5$–$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O⁻)$_2$), phosphinato (—P(O)(O⁻)), phospho (—PO$_2$), and phosphino (—PH$_2$); and the hydrocarbyl moieties $C_1$–$C_{24}$ alkyl (preferably $C_1$–$C_{12}$ alkyl, more preferably $C_1$–$C_6$ alkyl), $C_2$–$C_{24}$ alkenyl (preferably $C_2$–$C_{12}$ alkenyl, more preferably $C_2$–$C_6$ alkenyl), $C_2$–$C_{24}$ alkynyl (preferably $C_2$–$C_{12}$ alkynyl, more preferably $C_2$–$C_6$ alkynyl), $C_5$–$C_{24}$ aryl (preferably $C_5$–$C_{14}$ $_{aryl}$), $C_6$–$C_{24}$ alkaryl (preferably $C_6$–$C_{16}$ alkaryl), and $C_6$–$C_{24}$ aralkyl (preferably $C_6$–$C_{16}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "chiral" refers to a structure that does not have an improper rotation axis ($S_n$), i.e., it belongs to point group $C_n$ or $D_n$. Such molecules are thus chiral with respect to an axis, plane or center of asymmetry. Preferred "chiral" molecules herein are in enantiomerically pure form, such that a particular chiral molecule represents at least about 95 wt. % of the composition in which it is contained, more preferably at least about 99 wt. % of that composition.

The term "enantioselective" refers to a chemical reaction that preferentially results in one enantiomer relative to a second enantiomer, i.e., gives rise to a product of which a desired enantiomer represents at least about 50 wt. %. Preferably, in the enantioselective reactions herein, the desired enantiomer represents at least about 80 wt. % of the product, more preferably at least about 85 wt. % of the product, optimally at least about 95 wt. % of the product.

When a functional group, e.g., a hydroxyl, sulfhydryl, or amino group, is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene et al., *Protective Groups in Organic Synthesis* (New York: Wiley, 1991).

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

Accordingly, the invention provides a method for using organic catalysts to carry out an enantioselective aldol reaction using aldehydes as substrates, i.e., as both aldol donor and aldol acceptor, to provide a chiral β-hydroxy aldehyde in substantially enantiomerically pure form as an intermediate or final product. The catalyst is a nonmetallic chiral catalyst containing a Group 15 or Group 16 heteroatom, e.g., nitrogen, oxygen, sulfur or phosphorus, and a preferred heteroatom is nitrogen. Oxygen-containing and sulfur-containing catalysts may be, for example, alcohols and thiols, respectively, while phosphorus-containing catalysts will generally be phosphines. Heteroatom-containing activators in which the heteroatom is a nitrogen atom may be primary amines, secondary amines or nitrogen-containing polymers. Preferred amines are secondary amines having the structure of formula (III)

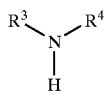

(III)

In formula (III), $R^3$ and $R^4$ are selected from the group consisting of hydrogen, hydrocarbyl (e.g., alkyl, alkenyl, alkynyl, aryl, alkaryl, alkaryl, etc.), substituted hydrocarbyl (e.g., substituted alkyl, alkenyl, alkynyl, aryl, alkaryl, alkaryl, etc.), heteroatom-containing hydrocarbyl (e.g., heteroatom-containing alkyl, alkenyl, alkynyl, aryl, alkaryl, alkaryl, etc.), and substituted heteroatom-containing hydrocarbyl (e.g., substituted heteroatom-containing alkyl, alkenyl, alkynyl, aryl, alkaryl, alkaryl, etc.), or $R^3$ and $R^4$ are taken together to form a substituted or unsubstituted ring structure optionally containing a further heteroatom in addition to the nitrogen atom shown in formula (III). When $R^3$ and $R^4$ are linked, the ring formed may be, for example, a five- or six-membered alicyclic or aromatic group, e.g., $R^3$ and $R^4$ may together form substituted or unsubstituted cyclopentyl, cyclohexyl, pyrrolidinyl, piperidinyl, morpholinyl, pyrrolyl, pyridinyl, pyrimidinyl, imidazolyl, or the like. Preferred compounds are those wherein $R^3$ and $R^4$ are independently selected from the group consisting of methyl, ethyl, propyl, butyl, cyclopentyl, cyclohexyl, cyclooctyl, phenyl, naphthyl, benzyl and trimethylsilyl, or are linked to form a 3- to 15-membered, optionally substituted cyclic moiety having the structure of formula (IV)

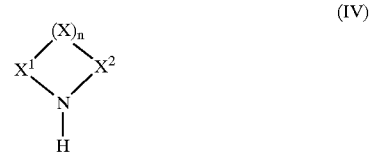

(IV)

wherein n is 0 or 1, X is a moiety that contains up to 50 atoms and is selected from the group consisting of hydrocarbylene, substituted hydrocarbylene, heteroatom-containing hydrocarbylene and substituted heteroatom-containing hydrocarbylene, and $X^1$ and $X^2$ are independently substituted or unsubstituted methylene. Exemplary such secondary amines have the structure of formula (V)

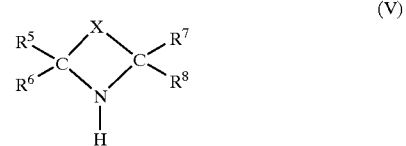

(V)

in which $R^5$, $R^6$, $R^7$, and $R^8$ are independently selected from hydrogen, hydroxyl, sulfhydryl, carboxyl, amino, mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, di-N-($C_1$–$C_{24}$ alkyl)-N-($C_5$–$C_{24}$ aryl)-substituted amino, $C_2$–$C_{24}$ alkylamido, $C_6$–$C_{24}$ arylamido, imino, $C_2$–$C_{24}$ alkylimino, $C_6$–$C_{24}$ arylimino, nitro, nitroso, $C_1$–$C_{24}$ alkoxy, $C_5$–$C_{24}$ aryloxy, $C_6$–$C_{24}$ aralkyloxy, $C_2$–$C_{24}$ alkylcarbonyl, $C_6$–$C_{24}$ arylcarbonyl, $C_2$–$C_{24}$ alkylcarbonyloxy, $C_6$–$C_{24}$ arylcarbonyl, $C_2$–$C_{20}$ alkoxycarbonyl, $C_6$–$C_{24}$ aryloxycarbonyl, halocarbonyl, carbamoyl, mono-($C_1$–$C_{24}$ alkyl)-substituted carbamoyl, di-($C_1$–$C_{24}$ alkyl)-substituted carbamoyl, di-N-($C_1$–$C_{24}$ alkyl)-N-($C_5$–$C_{24}$ aryl)-substituted carbamoyl, mono-($C_5$–$C_{24}$ aryl)-substituted carbamoyl, di-($C_5$–$C_{24}$ aryl)-substituted carbamoyl, thiocarbamoyl, mono-($C_1$–$C_{24}$ alkyl)-substituted thiocarbamoyl, di-($C_1$–$C_{24}$ alkyl)-substituted thiocarbamoyl, di-N-($C_1$–$C_{24}$ alkyl)-N-($C_5$–$C_{24}$ aryl)-substituted thiocarbamoyl, mono-($C_5$–$C_{24}$ aryl)-substituted thiocarbamoyl, di-($C_5$–$C_{24}$ aryl)-substituted thiocarbamoyl, carbamido, formyl, thioformyl, sulfo, sulfonato, $C_1$–$C_{24}$ alkylthio, $C_5$–$C_{24}$ arylthio, $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_2$–$C_{24}$ aralkyl, substituted $C_6$–$C_{24}$ aralkyl, $C_2$–$C_{24}$ heteroaralkyl, and substituted $C_2$–$C_{24}$ heteroaralkyl, or $R^5$ $R^6$, and/or $R^7$ and $R^8$, may together form an oxo moiety =O.

X may be, for example, -($CR^9R^{10}$)-($X^3$)$_q$-($CR^{11}R^{12}$)$_r$-, in which case the amine has the structure of formula (VI)

(VI)

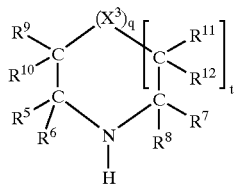

wherein $X^3$ is O, S, NH, $NR^{13}$, or $CR^{14}R^{15}$, q is zero or 1, t is zero or 1, and $R^9$, $R^{10}$, $R^{11}$, $R^{12}$, $R^{14}$, and $R^{15}$ are independently selected from hydrogen, hydroxyl, sulfhydryl, carboxyl, amino, mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, di-N-($C_1$–$C_{24}$ alkyl)-N-($C_5$–$C_{24}$ aryl)-substituted amino, $C_2$–$C_{24}$ alkylamido, $C_6$–$C_{24}$ arylamido, imino, $C_2$–$C_{24}$ alkylimino, $C_6$–$C_{24}$ arylimino, nitro, nitroso, $C_1$–$C_{24}$ alkoxy, $C_5$–$C_{24}$ aryloxy, $C_6$–$C_{24}$ aralkyloxy, $C_2$–$C_{24}$ alkylcarbonyl, $C_6$–$C_{24}$ arylcarbonyl, $C_2$–$C_{24}$ alkylcarbonyloxy, $C_6$–$C_{24}$ arylcarbonyloxy, $C_2$–$C_{20}$ alkoxycarbonyl, $C_6$–$C_{24}$ aryloxycarbonyl, halocarbonyl, carbamoyl, mono-($C_1$–$C_{24}$ alkyl)-substituted carbamoyl, di-($C_1$–$C_{24}$ alkyl)-substituted carbamoyl, di-N-($C_1$–$C_{24}$ alkyl)-N-($C_5$–$C_{24}$ aryl)-substituted carbamoyl, mono-($C_5$–$C_{24}$ aryl)-substituted carbamoyl, di-($C_5$–$C_{24}$ aryl)-substituted carbamoyl, thiocarbamoyl, mono-($C_1$–$C_{24}$ alkyl)-substituted thiocarbamoyl, di-($C_1$–$C_{24}$ alkyl)-substituted thiocarbamoyl, di-N-($C_1$–$C_{24}$ alkyl)-N-($C_5$–$C_{24}$ aryl)-substituted thiocarbamoyl, mono-($C_5$–$C_{24}$ aryl)-substituted thiocarbamoyl, di-($C_5$–$C_{24}$ aryl)-substituted thiocarbamoyl, carbamido, formyl, thioformyl, sulfo, sulfonato, $C_1$–$C_{24}$ alkylthio, $C_5$–$C_{24}$ arylthio, $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_2$–$C_{24}$ aralkyl, substituted $C_6$–$C_{24}$ aralkyl, $C_2$–$C_{24}$ heteroaralkyl, and substituted $C_2$–$C_{24}$ heteroaralkyl, or $R^9$ and $R^{10}$, and/or $R^{11}$ and $R^{12}$, together form an oxo moiety =O; and $R^{13}$ is selected from $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl.

In one preferred group of catalysts, q is zero, t is 1, and at least one of $R^5$ through $R^8$ is an acidic substituent such as a carboxyl group, such that the compound is proline or substituted proline. An exemplary catalyst is L-proline per se, which, as will be appreciated by those of ordinary skill in the art, corresponds to the structure of formula (VI) when $R^5$ through $R^7$ and $R^9$ through $R^{12}$ are hydrogen, and $R^8$ is β-carboxyl.

In another group of preferred catalysts, q is 1, $X^3$ is $NR^{13}$, t is zero, $R^5$ and $R^7$ are hydrogen, and $R^6$ is —$CR^{16}R^{17}R^{18}$, such that the secondary amine has the structure of formula (VIIA) or (VIIB)

(VIIA)

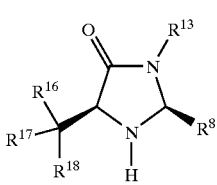

(VIIB)

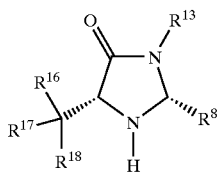

wherein the various substituents are as follows:

$R^8$ is as defined previously, and preferably has the structure -(L)$_m$—$CR^{19}R^{20}R^{21}$ wherein m is zero or 1, L is $C_1$–$C_6$ alkylene, and $R^{19}$, $R^{20}$ and $R^{21}$ are $C_1$–$C_{12}$ hydrocarbyl. More preferred $R^8$ substituents are those wherein m is zero and $R^{19}$, $R^{20}$ and $R^{21}$ are $C_1$–$C_{12}$ alkyl. Optimally, $R^{19}$, $R^{20}$ and $R^{21}$ are $C_1$–$C_6$ alkyl, e.g., methyl (such that $R^8$ is then a tert-butyl group).

$R^{13}$ is selected from $C_1$–$C_{12}$ hydrocarbyl (e.g., alkyl, alkenyl, alkynyl, aryl, alkaryl, aralkyl, etc.), substituted $C_1$–$C_{12}$ hydrocarbyl (e.g., substituted alkyl, alkenyl, alkynyl, aryl, alkaryl, aralkyl, etc.), heteroatom-containing $C_1$–$C_{12}$ hydrocarbyl (e.g., heteroatom-containing alkyl, alkenyl, alkynyl, aryl, alkaryl, aralkyl, etc.), and substituted heteroatom-containing $C_1$–$C_{12}$ hydrocarbyl (e.g., substituted heteroatom-containing alkyl, alkenyl, alkynyl, aryl, alkaryl, aralkyl, etc.). Preferred $R^{13}$ substituents are $C_1$–$C_{12}$ hydrocarbyl such as $C_1$–$C_{12}$ alkyl, with $C_1$–$C_6$ alkyl groups (e.g., methyl) particularly preferred.

$R^{16}$ and $R^{17}$ are independently selected from hydrogen, halo, hydroxyl, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl. Preferably, $R^{16}$ and $R^{17}$ are hydrogen or $C_1$–$C_{12}$ hydrocarbyl, and, optimally, $R^{16}$ and $R^{17}$ are both hydrogen.

$R^{18}$ is a cyclic group optionally substituted with 1 to 4 non-hydrogen substituents and containing zero to 3 heteroatoms generally selected from N, O, and S. In a preferred embodiment, $R^{18}$ is monocyclic aryl or heteroaryl optionally substituted with 1 to 4 substituents selected from halo, hydroxyl, and $C_1$–$C_{12}$ hydrocarbyl. More preferably, $R^{18}$ is phenyl optionally substituted with 1 or 2 substituents selected from halo, hydroxyl, and $C_1$–$C_6$ alkyl, and in a particularly preferred embodiment, $R^{18}$ is an unsubstituted phenyl group.

The catalysts are chiral with respect to an axis, plane or center of asymmetry, but are generally chiral with a center of asymmetry present. It will be appreciated by those skilled in the art that the various R groups discussed with respect to the foregoing amines can be selected to create the desired chirality.

Any of the aforementioned catalysts may also be employed in the present reactions in the form of an acid addition salt. That is, the catalyst may be incorporated into the reaction mixture as an acid addition salt, or an acid may be added to the reaction mixture to serve as a co-catalyst. The acid used to form the salt or employed as a co-catalyst for the electronically neutral compound is generally, although not necessarily, a Brønsted acid, preferably having a pKa of less than about 5. Combinations of Brønsted acids may also be used. Suitable acids include both organic and inorganic acids, with inorganic acids including, but not limited to, hydrochloric acid, hydrobromic acid, sulfuric acid, sulfurous acid, nitric acid, nitrous acid, perchloric acid, phosphoric acid, and chromic acid, and with organic acids exemplified by carboxylic acids, sulfonic acids, phosphonic acids, and aromatic alcohols, e.g., phenols, substituted with 1 to 5 electron-withdrawing substituents such as nitro, cyano, sulfonato, halo (i.e., Cl, F, Br or I) and halogenated alkyl (typically fluorinated alkyl, preferably perfluorinated lower alkyl such as trifluoromethyl). Particularly suitable organic acids are carboxylic acids and sulfonic acids having the structural formulas $R^x$—COOH and $R^x$—$SO_2$—OH wherein $R^x$ is aryl, alkyl, substituted aryl (e.g., halogenated aryl), or substituted alkyl (e.g., halogenated alkyl, particularly fluorinated and chlorinated alkyl). Preferred $R^x$ groups are methyl, halogenated methyl (e.g., fluorinated methyl such as trifluoromethyl, chlorinated methyl such as chloromethyl, dichloromethyl, and trichloromethyl, etc.), and nitrite-substituted methyl. Specific examples of preferred organic acids include acetic acid, propionic acid, glycolic acid, pyruvic acid, oxalic acid, malic acid, malonic acid, succinic acid, maleic acid, fumaric acid, tartaric acid, citric acid, benzoic acid, 2-nitrobenzoic acid, cinnamic acid, mandelic acid, methanesulfonic acid, ethanesulfonic acid, triflic acid, p-toluene sulfonic acid, salicylic acid, chloroacetic acid, dichloroacetic acid, trichloroacetic acid, trifluoroacetic acid, and combinations thereof. The Brønsted acid may or may not be chiral, and those Brønsted acids that are chiral may be used in isomerically pure form or as a racemic mixture.

Acid addition salts may be synthesized by admixing the electronically neutral form of the catalyst (e.g., an imidazolidinone of formula VIIA or VIIB) with a Brønsted acid $HX^A$, at a desired molar ratio, generally in the range of approximately 1:100 to 100:1, typically about 1:10 to 10:1, preferably about 1:2 to 2:1. Alternatively, the uncharged catalyst may be combined with at least one salt $[M^{z+}]_z[X^A]^-$, thereby forming the desired salt via ion exchange. A wide variety of salts may be used for this latter purpose, and the cation $M^{+z}$ can be virtually any cation, although z is generally 1, 2 or 3. Suitable M elements are typically chosen from Groups 2 to 13 of the Periodic Table of the Elements, but M may also be a polyatomic cation such as the ammonium ion $NH_4^+$. It should also be noted that the salt form of the catalyst can be prepared with two or more different Brønsted acids or metal salts, thereby forming a mixture of salts, i.e., salts containing different anions $[X^A]^-$.

The product of the catalyzed aldol coupling reaction of the invention depends, of course, on the particular aldehyde reactant(s) and the specific catalyst used. In one embodiment, the only reactant is an enolizable aldehyde, and the aldol coupling reaction can proceed so as to dimerize the aldehyde, trimerize the aldehyde, or polymerize the aldehyde. Any enolizable aldehyde may be employed, meaning that the sole requirement of the aldehyde is that the α-carbon contain a single enolizable hydrogen atom. The α-carbon may be substituted with one or two nonhydrogen substituents that may be the same or different, e.g., a hydrocarbyl, substituted hydrocarbyl, heteroatom-containing hydrocarbyl, substituted heteroatom-containing hydrocarbyl, or functional group. Preferred enolizable aldehydes contain one substituent at the α-carbon and have the structure of formula (I)

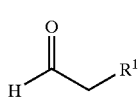

(I)

wherein $R^1$ is selected from hydrocarbyl, substituted hydrocarbyl, heteroatom-containing hydrocarbyl, substituted heteroatom-containing hydrocarbyl, and functional groups, and is preferably selected from $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_6$–$C_{24}$ aralkyl, substituted $C_6$–$C_{24}$ aralkyl, $C_2$–$C_{24}$ heteroaralkyl, and substituted $C_2$–$C_{24}$ heteroaralkyl. Optimally, $R^1$ is selected from $C_1$–$C_{12}$ alkyl, substituted $C_1$–$C_{12}$ alkyl, $C_1$–$C_{12}$ heteroalkyl, substituted $C_1$–$C_{12}$ heteroalkyl, $C_5$–$C_{14}$ aryl, substituted $C_5$–$C_{14}$ aryl, $C_3$–$C_{14}$ heteroaryl, substituted $C_3$–$C_{14}$ heteroaryl, $C_6$–$C_{16}$ aralkyl, substituted $C_6$–$C_{16}$ aralkyl, $C_3$–$C_{16}$ heteroaralkyl, and substituted $C_3$–$C_{16}$ heteroaralkyl.

Typically, a more acidic catalyst, e.g., proline, will result in dimerization, while a less acidic catalyst, e.g., an imidazolidinone of formula (VIIA) or (VIIB), will result in trimerization. These reactions are illustrated in Schemes 3 and 4, below:

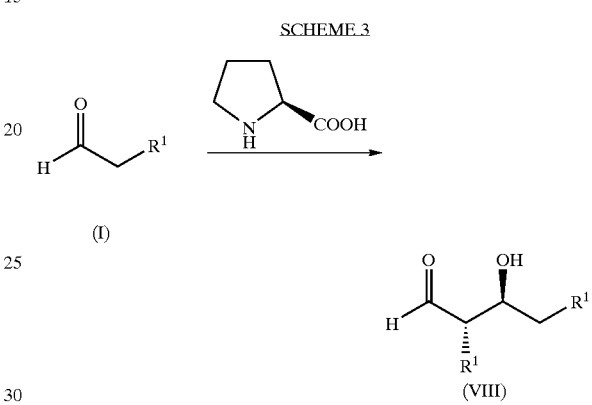

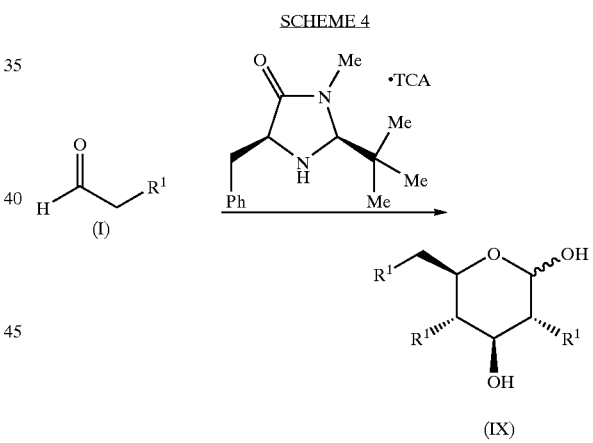

In the above schemes, "Me" represents methyl, "Ph" represents phenyl, and "TCA" represents trichloroacetic acid (such that the catalyst shown in Scheme 4 is in the form of the trichloroacetate salt). Specific reactions of Schemes 3 and 4, wherein $R^1$ is methyl (such that the enolizable aldehyde is propionaldehyde), are described in Examples 1 and 8.

It will be appreciated that the tetrahydropyran (VIII) and the β-hydroxy aldehyde (IX) may be subjected to further reaction, depending upon the ultimate product desired. The further reaction may, in most cases, be carried out in the context of a "one-pot synthesis," without isolation or purification of (VIII) or (IX). Examples of further reactions that may be carried out to modify reaction products (VIII) and (IX) include reduction with a suitable reducing agent (e.g., sodium borohydride) to convert carbonyl moieties to hydroxyl groups, hydrogenation in the presence of an alcoholic acid (e.g., CSA in methanol) to convert hydroxyl groups to ethers, additional aldol coupling reactions with aldehydes or ketones, and the like.

In another embodiment, the aldol coupling reaction is carried out with an enolizable aldehyde as described above, e.g., having the structure of formula (I), and an additional aldehyde, such that aldol coupling is a "cross-aldol" reaction in which the α-carbon of the enolizable aldehyde undergoes nucleophilic addition to the carbonyl carbon of the additional aldehyde. The second aldehyde may or may not be enolizable, and is generally represented by formula (II)

(II)

in which $R^2$ is selected from hydrocarbyl, substituted hydrocarbyl, heteroatom-containing hydrocarbyl, and substituted heteroatom-containing hydrocarbyl, and is preferably selected from $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_6$–$C_{24}$ aralkyl, substituted $C_6$–$C_{24}$ aralkyl, $C_2$–$C_{24}$ heteroaralkyl, and substituted $C_2$–$C_{24}$ heteroaralkyl, and is most preferably selected from $C_1$–$C_{12}$ alkyl, substituted $C_1$–$C_{12}$ alkyl, $C_1$–$C_{12}$ heteroalkyl, substituted $C_1$–$C_{12}$ heteroalkyl, $C_5$–$C_{14}$ aryl, substituted $C_5$–$C_{14}$ aryl, $C_3$–$C_{14}$ heteroaryl, substituted $C_3$–$C_{14}$ heteroaryl, $C_6$–$C_{16}$ aralkyl, substituted $C_6$–$C_{16}$ aralkyl, $C_3$–$C_{16}$ heteroaralkyl, and substituted $C_3$–$C_{16}$ heteroaralkyl.

These aldol coupling reactions involving two or more nonidentical aldehydes are illustrated in the schemes below. Schemes 5 and 6 show aldol coupling reactions of the invention wherein one of the aldehyde reactants is enolizable and the second is nonenolizable (wherein approximately one equivalent of each aldehyde is employed in Scheme 5, and two equivalents of the nucleophilic aldehyde are employed in Scheme 6), and Scheme 7 illustrates an aldol coupling reaction of the invention using two enolizable aldehyde reactants.

SCHEME 5

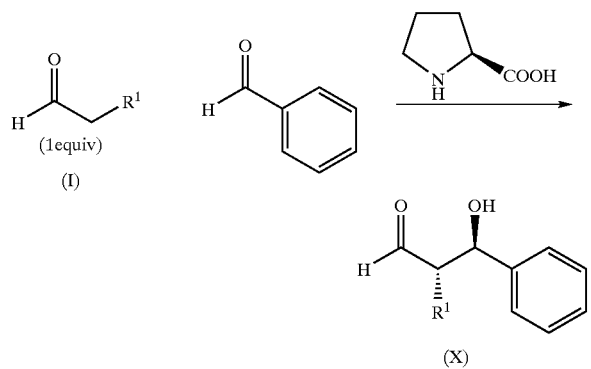

SCHEME 6

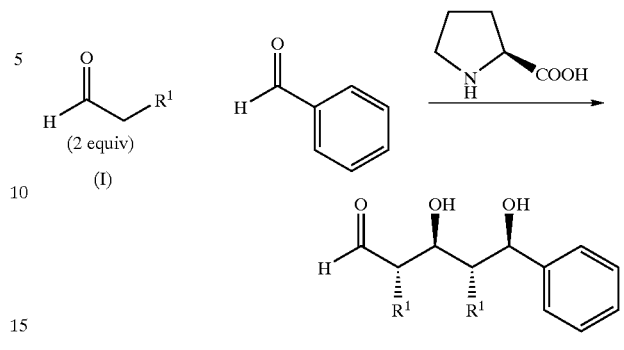

SCHEME 7

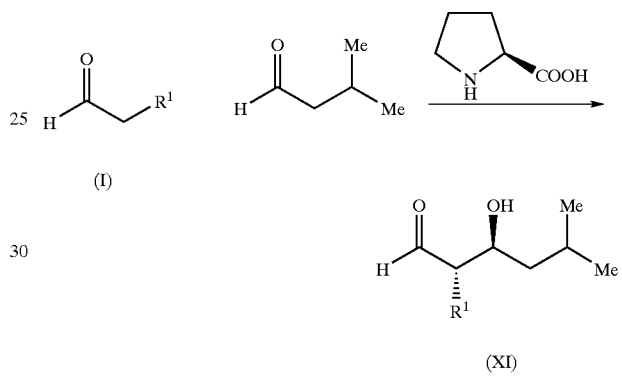

A reaction encompassed by Scheme 5, in which aldol coupling involves the addition of propionaldehyde to benzaldehyde (i.e., $R^1$ is methyl), is described in Example 4. A reaction analogous to that of Scheme 6 is described in Example 9. A reaction of Scheme 7, wherein aldol coupling involves the addition of propionaldehyde to isovaleraldehyde, both enolizable aldehydes, is described in Example 5. As indicated above, further reactions may be carried out to modify the β-hydroxy aldehydes (X) and (XI) as desired.

As documented in the examples, aldol coupling reactions of aldehydes in the presence of nonmetallic, chiral organic catalysts as described herein proceed in a synthetically straightforward manner with excellent levels of enantioselectivity.

The method of the invention may be applied to the synthesis of saccharides or analogs thereof, including monosaccharides, disaccharides, and polysaccharides. In this embodiment, the aldol coupling reaction is carried out with at least one enolizable aldehyde of formula (I) wherein $R^1$ is a protected hydroxyl, sulfhydryl, or amino group, typically a protected hydroxyl group. Suitable protecting groups will be known to those of ordinary skill in the art and are described in the pertinent texts and literature; see Greene, supra. Non-limiting examples of hydroxyl-protecting groups useful in this embodiment include, without limitation: silyl moieties, such as trialkylsilyl (e.g., triisopropylsilyl, or "TIPS"; trimethylsilyl, or "TMS") moieties, which form silyl ethers; benzyl ("Bn") and substituted benzyl moieties such as p-methoxybenzyl ("PBN"), which form benzyl ethers; and acyl moieties, such as acetyl, which form esters, such as acetyl ("Ac") groups.

For example, trimerization of O-protected hydroxyaldehyde will give rise to the tetrahydropyran of formula (VIII) wherein $R^1$ is protected hydroxyl (—O—Pr where Pr is a protecting group), which corresponds to a protected glucose molecule:

SCHEME 8

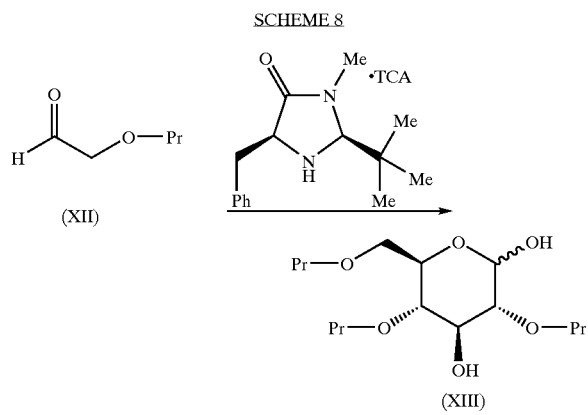

The protecting groups may be removed using conventional reagents and methods to give the unprotected monosaccharide. Trimerization using two different aldehydes H—(CO)—CH$_2$—Pr$^1$ and H—(CO)—Pr$^2$—where Pr$^1$ and Pr$^2$ are orthogonally removable protecting groups such as benzyl and acetyl—will result in a bis-differentially protected glucose molecule, where further reactions may then be conducted by removing one but not both protecting groups and reacting the initially unprotected group(s) prior to removal of the second protecting group.

Any of the reactions herein can be carried out on a solid support, using solid phase synthesis techniques. Solid-phase synthesis enables implementation of the present aldol coupling reaction in combinatorial chemistry processes, wherein an array or "matrix" of reactions are conducted in parallel on a single substrate. In such a case, the catalyst itself can be bound either directly or indirectly to the surface of a solid substrate, if indirectly, through a cleavable or noncleavable linker. For example, the catalyst of formula (VIIA) or (VIIB) can be linked to the surface of a substrate through any of $R^8$, $R^{13}$, or $R^{16}$ through $R^{17}$. Any solid support may be used. Typical substrates are those conventionally used in solid phase chemistry and which allow for chemical synthesis thereon. The only limitation upon the materials useful for constructing substrates is that they must be compatible with the reaction conditions to which they are exposed. Suitable substrates useful in practicing the methods of the invention include, but are not limited to, organic and inorganic polymers (e.g., polyethylene, polypropylene, polystyrene, polytetrafluoroethylene), metal oxides (e.g., silica, alumina), mixed metal oxides, metal halides (e.g., magnesium chloride), minerals, quartz, zeolites, and the like. Other substrate materials will be apparent to those of skill in the art.

Process conditions: The catalytic aldol coupling reactions of the invention are generally carried out in a solvent, typically a nonpolar organic solvent, although the specific solvent will depend, of course, on the nature of the reactants, i.e., on any substituents present on the aldehyde(s). Ideally, the solvent selected allows retention and regeneration of the catalyst and removal of the reaction product following completion of the reaction. Examples of suitable solvents include, without limitation, benzene, chloroform, ethyl acetate, tetrahydrofuran, dioxane, acetonitrile, dimethylsulfoxide, N-methylpyrrolidone, and dimethyl formamide. The aldol coupling reaction may be carried out in batch, semi-continuously or continuously, in air or an inert atmosphere, at autogenous pressure or higher, depending, for example, on the nature of the catalyst composition and reactants used. The reaction temperature will generally be in the range of about −100° C. to 100° C., preferably in the range of about −90° C. to 50° C. Lower temperatures, in the range of about 0° C. to about 10° C., generally result in a higher yield and greater enantioselectivity.

The amount of catalyst is generally in the range of about 0.1 mole % to 1 stoichiometric equivalent, preferably in the range of about 1 mol % to 20 mole %, and the molar ratio of the aldehydes within the reaction mixture will depend on the desired product. For most coupling reactions, wherein a straightforward coupling is desired between two or more aldehydes, approximately one equivalent of each aldehyde will be used. Industrially, the reaction may be scaled up to 10,000 gallons or more. Catalysis may be heterogeneous or homogeneous. It will be appreciated by those skilled in the art of catalysis that the aforementioned process conditions may vary depending on the particular reaction, the desired product, the equipment used, and the like. Generally, the reaction product is obtained after completion of the reaction, wherein an optional extraction and/or catalyst recovery step and/or drying is followed by concentration or distillation to give the crude product and purification, e.g., by chromatography, sublimation, precipitation, extraction, crystallization with optional seeding and/or co-crystallization aids. Alternatively, the reaction product— e.g., a β-hydroxy aldehyde—may be immediately subjected to further reaction without first being isolated and purified.

It is to be understood that while the invention has been described in conjunction with the preferred specific embodiments thereof, that the description above as well as the examples that follow are intended to illustrate and not limit the scope of the invention. Other aspects, advantages and modifications within the scope of the invention will be apparent to those skilled in the art to which the invention pertains.

All patents, patent applications, journal articles and other reference cited herein are incorporated by reference in their entireties.

Experimental

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

Commercial reagents were purified prior to use following the guidelines of Perrin and Armarego, *Purification of Laboratory Chemicals*, Fourth Edition (Oxford, Butterworth-Heinemann, 1996). Dimethylformamide was obtained from EM Science in a DriSolv™ container and used as supplied. Nonaqueous reagents were transferred under nitrogen or cannula. Organic solutions were concentrated under reduced pressure on a Büchi rotary evaporator using an ice-water bath. Chromatographic purification of products was accomplished using forced-flow chromatography on ICN 60 32-64 mesh silica gel 63 according to the method of Still et al. (1978) *J. Org. Chem.* 43:2923. Thin-layer chromatography (TLC) was performed on EM Reagents 0.25 mm silica gel 60-F plates. Visualization of the developed chromatogram was performed by fluorescence quenching or by anisaldehyde stain. Known catalyst ((5S)-5-benzyl-2,2,3-trimethylimidazolidin-4-one and (2S,5S)-5-benzyl-2-tert-butyl-3-methylimidazolidin-4-one, respectively) was prepared as described in U.S. Pat. No. 6,369,243 to MacMillan et al.

$^1$H and $^{13}$C NMR spectra were recorded on a Mercury 300 spectrometer (300 MHz and 75 MHz), and are internally referenced to residual protio solvent signals. Data for $^1$H NMR are reported as follows: chemical shift (δ ppm), multiplicity (s=singlet, d=doublet, t=triplet, q=quartet, m=multiplet, br=broad), coupling constant (Hz), integration and assignment. Data for $^{13}$C NMR are reported in terms of chemical shift (δ ppm). IR spectra were recorded on a Perkin Elmer Paragon 1000 spectrometer and are reported in terms of frequency of absorption (cm$^{-1}$). Mass spectra were obtained from the UC Irvine Mass Spectral facility. Gas liquid chromatography (GLC) was performed on Hewlett-Packard 6850 and 6890 Series gas chromatographs equipped with a split-mode capillary injection system and flame ionization detectors using a Bodman Chiraldex β-DM (30 m×0.25 mm) column or an ASTEC Chiraldex γ-BP (30 m×0.25 mm) as noted. High performance liquid chromatography (HPLC) was performed on Hewlett-Packard 1100 Series chromatographs using a Chiralcel AD column (25 cm) or a Chiralcel OJ column (25 mm) and OJ guard (5 cm) as noted. Optical rotations were taken using a Jasco P-1010 polarimeter (WI lamp, 589 nm, 25° C.).

Examples 1 through 11 describe the use of the chiral organic catalysts L-proline and (2S,5S)-5-benzyl-2-tert-butyl-3-methylimidazolidin-4-one in catalyzing the direct and enantioselective aldol coupling reaction of aldehyde substrates.

EXAMPLE 1

Synthesis of (2S, 3S)-3-hydroxy-2-methylpentanal (Table 1, entry 1): A suspension of freshly distilled propionaldehyde (3.61 mL, 50 mmol) and l-proline in 25.0 mL of dimethylformamide was stirred at 4° C. for 10 h. The resulting solution was diluted with diethyl ether and washed successively with water and brine. The combined aqueous layers were back-extracted with 3 portions of dichloromethane. The organic layers were combined, dried over anhydrous MgSO$_4$, and concentrated in vacuo. Flash chromatography (5:2 pentane:diethyl ether) afforded the title compound as a clear, colorless oil in 80% yield (2.31 g, 20 mmol), 99% ee, and 4:1 anti:syn. Analytical data for this compound are identical in every respect to previously reported values (Mahrwald (1998) *Synthesis*, 262), with the exception of optical rotation which has not been reported. [α]D=−14.7 (c=1.0, CHCl3). The product ratios were determined by GLC analysis of the acetal derived from 2,2-dimethylpropane-1,3-diol, obtained by the method of Yamamoto (Furuta et al. (1989) *J. Org. Chem.* 54:1481), using a Bodman Chiraldex γ-DM (30 m×0.25 mm) column (110° C. isotherm, 23 psi); (2S, 3S) anti isomer tr=24.6 min, (2R, 3R) anti isomer tr=25.5 min, (2R, 3S) and (2S, 3R) syn isomers tr=22.4 min.

EXAMPLE 2

Synthesis of (2S, 3S)-3-hydroxy-2,5-dimethylhexanal (Table 1, entry 2): A solution of freshly distilled propionaldehyde (144 μL, 2.0 mmol) in 500 μL dimethylformamide pre-cooled to 4° C. was added slowly over the course of 2.5 h to a stirring suspension of isovaleraldehyde (107 μL, 1.0 mmol), L-proline (11.5 mg, 0.10 mmol) and 500 μL dimethylformamide at 4° C. After 16 h, the resulting solution was diluted with diethyl ether and washed successively with water and brine. The combined aqueous layers were back-extracted with 3 portions of dichloromethane. The organic layers were combined, dried over anhydrous MgSO$_4$, and concentrated in vacuo. Flash chromatography (20:7 pentane:diethyl ether) afforded the title compound as a clear, colorless oil in 88% yield (126 mg, 0.88 mmol), 97% ee and 3:1 anti:syn. IR (film) 3419, 2958, 2935, 2872, 1719,1466, 1368, 1152, 1098, 1062,1025, 976.5 cm$^{-1}$; $^1$H NMR (300 MHz, CDCl$_3$) δ9.75 (d, J=1.5 Hz, 1H, CHO); 3.89 (ddd, 1H, J=9.9, 6.6, 2.7 Hz, 1H, CHOH); 2.44 (m, 1H, CHCH$_3$); 1.83 (m, 1H, CH(CH$_3$)$_2$); 1.47 (m, 1H, CH$_2$); 1.26 (m, 1H, CH$_2$); 1.14 (d, 3H, J=7.2 Hz, CH$_3$CHCHO); 0.97 (d, 3H, J=5.1 Hz, (CH$_3$)$_2$CH); 0.92 (d, 3H, J=6.6 Hz, (CH$_3$)$_2$CH); $^{13}$C NMR (75 MHz, CDCl$_3$) δ205.5, 70.9, 52.8, 44.0, 34.5, 24.1, 21.8, 11.1; HRMS (CI) exact mass calcd for [M +H]$^+$ (C$_8$H$_{17}$O$_2$) requires m/z 145.1228, found m/z 145.1225; [α]$_D$=−33.6 (c=1.0, CHCl$_3$). The product ratios were determined by GLC analysis of the acetal derived from 2,2-dimethylpropane-1,3-diol (obtained by the method of Yamamoto, supra) using a Bodman Chiraldex β-DM (30 m×0.25 mm) column (100° C. isotherm, 23 psi); (2S, 3S) anti isomer t$_r$=50.8 min, (2R, 3R) anti isomer t$_r$=53.2 min, (2R, 3S) and (2S, 3R) syn isomers t$_r$=45.5 min.

EXAMPLE 3

Synthesis of (2S, 3S)-3-cyclohexyl-3-hydroxy-2-methylpropanal (Table 1, entry 3): A solution of freshly distilled propionaldehyde (72 μL, 1.0 mmol) in 500 μL dimethylformamide pre-cooled to 4° C. was added slowly over the course of 20 h to a stirring suspension of cyclohexane carboxaldehyde (242 μL, 2.0 mmol), L-proline (11.5 mg, 0.10 mmol) and 500 μL dimethylformamide at 4° C. After 22 hours, the resulting solution was diluted with diethyl ether and washed successively with water and brine. The combined aqueous layers were back-extracted with 3 portions dichloromethane. The organic layers were combined, dried over anhydrous MgSO$_4$, and concentrated in vacuo. Flash chromatography (20:7 pentane:diethyl ether) afforded the title compound as a clear, colorless oil in 87% yield (148 mg, 0.87 mmol), 99% ee and 93:7 anti:syn. IR (film) 3438, 2928, 2853, 1722, 1450, 1396, 1376, 1314, 1186, 1112, 1063, 975.8, 893.2, 847.5 cm$^{-1}$; $^1$H NMR (300 MHz, CDCl$_3$) δ9.75 (d, 1H, J=2.1 Hz, CHO); 3.53 (dd, 1H, J=7.2, 4.8 Hz, CHOH); 2.58 (m, 1H, CHCH$_3$); 1.8-1.0 (br m, 11H, cyclohexyl); 1.10 (d, 3H, J=7.2 Hz, CH$_3$); $^3$C NMR (75 MHz, CDCl$_3$) δ206.1, 77.1, 49.2, 40.7, 30.3, 26.73, 26.69, 26.68, 26.4, 11.4; HRMS (CI) exact mass calcd for [M+H]$_+$ (C$_{10}$H$_{19}$O$_2$) requires m/z 171.1385, found m/z 171.1386. [α]$_D$=−5.1 (c=1.0, CHCl$_3$). The product ratios were determined by GLC analysis of the corresponding 4-cyclohexyl-2,2,5-trimethyl-[1,3]dioxane (obtained by NaBH$_4$ reduction followed by acetonide protection of the 1,3-diol according to the method of Goto, in Kitamura et al. (1984) *J. Am. Chem. Soc.* 106:3252) using a Bodman Chiraldex β-DM (30 m×0.25 mm) column (110° C. isotherm, 23 psi); (2S, 3S) anti isomer t$_r$=17.8 min, (2R, 3R) anti isomer t$_r$=18.7 min, (2R, 3S) and (2S, 3R) syn isomers t$_r$=21.0, 22.2 min.

Stereochemical analysis: The absolute stereochemistry of (2S, 3S)-3-Cyclohexyl-3-hydroxy-2-methylpropanal was determined by correlation to (2S, 3S)-3-cyclohexyl-3-hydroxy-2-methylpropionic acid methyl ester, as follows. A stirring solution of (2S, 3S)-3-cyclohexyl-3-hydroxy-2-methylpropanal (77 mg, 0.45 mmol) in 3.0 mL of ethanol was treated sequentially with a solution of AgNO$_3$ (123 mg, 0.73 mmol) in 2.0 mL of water and a solution of NaOH (123 mg, 3.1 mmol) in 3.0 mL of 2:1 ethanol:water. After stirring for 4 hours, the mixture was filtered through celite, and the filter cake was rinsed with several portions of ethyl acetate. The filtrate was then washed with 1N HCl and the aqueous layer was back-extracted with ethyl acetate. The combined organic extracts were dried over anhydrous $Na_2SO_4$, filtered, and concentrated in vacuo. The residue was then dissolved in 8.0 mL of methanol and trimethylsilyldiazomethane (2.0 M in hexane) was added until a yellow color persisted. Excess diazomethane was quenched by the dropwise addition of acetic acid. The resulting colorless solution was then diluted with ether, washed successively with 10% $NaHCO_3$ and brine, dried over anhydrous $MgSO_4$, and concentrated in vacuo. Flash chromatography (5–10% ethyl acetate in hexanes, linear gradient) afforded a 71% yield (63 mg, 0.32 mmol) of (2S, 3S)-3-cyclohexyl-3-hydroxy-2-methylpropionic acid methyl ester; $[\alpha]_D$=+5.1 (c=1.05, $CHCl_3$) (lit.$[\alpha]_D$=−8.1 (c=1.05, $CHCl_3$) for (2R, 3R)-3-cyclohexyl-3-hydroxy-2-methylpropionic acid methyl ester; Meyers et al. (1981) *J. Am. Chem. Soc.* 103:4278).

EXAMPLE 4

Synthesis of (2S, 3S)-3-hydroxy-2-methyl-3-phenylpropionaldehyde (Table 1, entry 4): A solution of freshly distilled propionaldehyde (72 µL, 1.0 mmol) in 500 µL dimethylformamide pre-cooled to 4° C. was added slowly over the course of 16 h to a stirring suspension of benzaldehyde (1.02 mL, 10 mmol), L-proline (11.5 mg, 0.10 mmol) and 4.5 mL dimethylformamide at 4° C. After 16 hours, the resulting solution was diluted with ethyl acetate and washed successively with water and brine. The combined aqueous layers were back-extracted with 3 portions of dichloromethane. The organic layers were combined, dried over anhydrous $Na_2SO_4$, and then concentrated. Flash chromatography (4:1 hexanes:ethyl acetate) afforded the title compound as a clear, colorless oil in 81% yield (132 mg, 0.81 mmol), 99% ee and 3:1 anti:syn. Analytical data for this compound are identical in every respect to that previously reported (Mahrwald, supra) with the exception of optical rotation which has not been reported. $[\alpha]_D$=+9.1 (c=1.0, $CHCl_3$). The product ratios were determined by HPLC analysis of the corresponding alcohol (obtained by $NaBH_4$ reduction) using a Chiracel AD and AD guard column (1.0% isopropanol/hexanes, 1 mL/min); (2S, 3S) anti isomer $t_r$=147.5 min, (2R, 3R) anti isomer $t_r$=161.1 min, (2R, 3S) and (2S, 3R) syn isomers $t_r$=173.0, 200.0 min.

EXAMPLE 5

(2S, 3S)-3-hydroxy-2,4-dimethylpentanal (Table 1, entry 5). A solution of freshly distilled propionaldehyde (1.81 mL, 25.0 mmol) in 12.5 mL dimethylformamide pre-cooled to 4° C. was added slowly over the course of 20 h to a stirring suspension of isobutyraldehyde (4.54 mL, 50 mmol), L-proline (288 mg, 2.5 mmol) and 12.5 mL dimethylformamide at 4° C. After 30 h, the resulting solution was diluted with diethyl ether and washed successively with water and brine. The combined aqueous layers were back-extracted with 3 portions of dichloromethane. The organic layers were combined, dried over anhydrous $MgSO_4$, and concentrated in vacuo. Flash chromatography (20:7 pentane:diethyl ether) afforded the title compound as a clear, colorless oil in 82% yield (2.65 g, 20.6 mmol), >99% ee and 96:4 anti:syn. Analytical data for this compound are identical in every respect to the previously reported values (Mahrwald, supra), with the exception of optical rotation which has not been reported. $[\alpha]_D$=−17.9 (c=1.0, $CHCl_3$). The product ratios were determined by GLC analysis of the acetal derived from 2,2-dimethylpropane-1,3-diol (obtained by the method of Yamamoto) using a Bodman Chiraldex β-DM (30 m×0.25 mm) column (110° C. isotherm, 23 psi); (2S, 3S) anti isomer $t_r$=31.8 min, (2R, 3R) anti isomer $t_r$=33.9 min, (2R, 3S) and (2S, 3R) syn isomers $t_r$=29.4, 29.8 min.

Stereochemical analysis: The absolute stereochemistry of (2S, 3S)-3-hydroxy-2,4-dimethylpentanal was determined by correlation to (2S, 3S)-3-hydroxy-2,4-dimethylpentanoic acid methyl ester, as follows. A stirring solution of (2S, 3S)-3-hydroxy-2,4-dimethylpentanal (101 mg, 0.63 mmol) in 3.0 mL of ethanol was treated sequentially with a solution of $AgNO_3$ (170 mg, 1.0 mmol) in 2.0 mL of water and a solution of NaOH (171 mg, 4.3 mmol) in 3.0 mL of 2:1 ethanol:water. After stirring for 4 hours, the mixture was filtered through celite, and the filter cake was rinsed with several portions of ether. The filtrate was then washed with 1N HCl and the aqueous layer was back-extracted with ether. The combined organic extracts were dried over anhydrous $MgSO_4$, filtered, and concentrated in vacuo. The residue was then dissolved in 8.0 mL of methanol, and trimethylsilyldiazomethane (2.0 M in hexane) was added until a yellow color persisted. Excess diazomethane was quenched by the dropwise addition of acetic acid. The resulting colorless solution was then diluted with ether, washed successively with 10% $NaHCO_3$ and brine, dried over anhydrous $MgSO_4$, and concentrated in vacuo. Flash chromatography (5–25% ether in pentane, linear gradient) afforded a 39% yield (47 mg, 0.25 mmol) of (2S, 3s)-3-hydroxy-2,4-dimethylpentanoic acid methyl ester; $[\alpha]_D$=+7.6 (c=0.85, $CHCl_3$) (lit.$[\alpha]_D$=+11.1 (c=0.85, $CHCl_3$; Oppolzer et al. (1991) *Tet. Lett.* 32:61).

EXAMPLE 6

Synthesis of (2S)-2-[(1S)-1-hydroxy-2-methylpropyl] hexanal (Table 1, entry 6): A solution of freshly distilled hexanal (120 µL, 1.0 mmol) in 500 µL dimethylformamide was added slowly over the course of 24 h to a stirring suspension of isobutyraldehyde (272 µL, 3.0 mmol), L-proline (11.5 mg, 0.10 mmol) and 500 µL dimethylformamide at room temperature. After 24 h, the resulting solution was diluted with diethyl ether and washed successively with water and brine. The combined aqueous layers were back-extracted with 3 portions dichloromethane. The organic layers were combined, dried over anhydrous $MgSO_4$, and concentrated in vacuo. Flash chromatography (7:3 pentane:diethyl ether) afforded the title compound as a clear, colorless oil in 80% yield (127 mg, 0.80 mmol), 98% ee and 96:4 anti:syn. IR (film) 3458, 2960, 2934, 2874, 2725, 1720, 1467, 1328, 1220, 1146, 1024, 991.2, 959.9, 901.1, 775.6 $cm^{-1}$; $^1H$ NMR (300 MHz, $CDCl_3$) δ9.75 (d, 1H, J=3.3 Hz, CHO); 3.56 (dd (apparent q), 1H, J=6.0, 5.7 Hz, CHOH); 2.46 (dddd, 1H, J=8.4, 5.7, 5.7, 3.3 Hz, $CHCH_2$); 1.99 (d, 1H, J=6.0 Hz, OH); 1.82 (m, 1H, $CH(CH_3)_2$); 1.70 (m, 1H, $CHCH_2$); 1.58 (m, 1H, $CHCH_2$); 1.30 (m, 4H, $CH_2CH_2CH3$); 0.97 (d, 3H, J=6.6 Hz, $CH(CH_3)_2$); 0.93 (d, 3H, J=6.6 Hz, $CH(CH_3)_2$); 0.90 (dd (apparent t), 3H, J=6.6, 6.6 Hz); $^{13}C$ NMR (75 MHz, $CDCl_3$) δ206.1, 76.7, 54.9, 31.3, 29.5, 26.7, 23.2, 20.0, 17.1, 14.2; HRMS (CI) exact mass calcd for $[M+H]^+$ ($C_{10}H_{21}O_2$) requires m/z 173.1541, found m/z 173.1540; $[\alpha]_D$=−15.4 (c=1.0, $CHCl_3$). The product ratios were determined by GLC analysis of the acetal derived from 2,2-dimethylpropane-1,3-diol (obtained by the method of Yamamoto, supra) using a Bodman Chiraldex β-DM (30 m×0.25 mm) column (110° C. isotherm, 23 psi); (2S, 3S) anti isomer $t_r$=97.8 min, (2R, 3R) anti isomer $t_r$=102.7 min, (2R, 3S) and (2S, 3R) syn isomers $t_r$=94.4, 96.5 min.

EXAMPLE 7

Synthesis of (2S, 3S)-2-benzyl-3-hydroxy-4-methylpentanal (Table 1, entry 7): A solution of freshly distilled hydrocinnamaldehyde (132 μL, 1.0 mmol) in 500 μL dimethylformamide was added slowly over the course of 24 h to a stirring suspension of isobutyraldehyde (272 μL, 3.0 mmol), L-proline (11.5 mg, 0.10 mmol) and 500 μL dimethylformamide at room temperature. After 26 h, the resulting solution was diluted with ethyl acetate and washed successively with water and brine. The combined aqueous layers were back-extracted with 3 portions dichloromethane. The organic layers were combined, dried over anhydrous $Na_2SO_4$, and concentrated in vacuo. Flash chromatography (3:1 hexanes:ethyl acetate) afforded the title compound as a clear, colorless oil in 75% yield (155 mg, 0.75 mmol), 91% ee and 95:5 anti:syn. IR (film) 3466, 3086, 3063, 3028, 2962, 2932, 2834, 2733, 1950, 1875, 1806, 1722, 1604, 1496, 1454, 1390, 1368, 1244, 1180, 1136, 1049, 1031, 993.0, 964.3, 849.7, 800.6, 739.8, 700.2 cm$^{-1}$; $^1$H NMR (300 MHz, CDCl$_3$) δ9.83 (d, 1H, J=2.1 Hz, CHO); 7.27 (m, 5H, Ar—H); 3.43 (ddd, 1 H, J=6.6, 6.6, 4.5 Hz, CHOH); 3.06 (dd, 1H, J=13.2, 7.8 Hz, PhCH$_2$); 2.92 (dd, 1H, J=13.2, 6.9 Hz, PhCH$_2$); 2.81 (m, 1H, CHCH$_2$); 2.15 (d, 1H, J=6.0 Hz, OH); 1.90 (m, 1H, CH(CH$_3$)$_2$); 0.96 (d, 3H, J=6.6 Hz, CH(CH$_3$)$_2$); 0.92 (d, 3H, J=7.2 Hz, CH(CH$_3$)$_2$); $^{13}$C NMR (75 MHz, CDCl$_3$) δ205.6, 129.2, 128.9, 128.6, 126.8, 76.9, 55.8, 33.4, 32.0, 19.7, 18.2; HRMS (CI) exact mass calcd for [M+H]$^+$ (C$_{13}$H$_{19}$O$_2$) requires m/z 207.1385, found m/z 207.1386; [α]$_D$=−7.9 (c=1.0, CHCl$_3$). The product ratios were determined by HPLC analysis of the corresponding alcohol (obtained by NaBH$_4$ reduction) using a Chiracel OJ and OJ guard column (1.0% ethanol/hexanes, 1 mL/min); (2S, 3S) anti isomer t$_r$=7.5 min, (2R, 3R) anti isomer t$_r$=9.4 min, (2R, 3S) and (2S, 3R) syn isomers t$_r$=6.3, 6.9 min.

The conditions, yield, and enantioselectivity for the reactions of Examples 1 through 7 are summarized in Table 1:

TABLE 1

| entry | R$^1$ | R$^2$ | Product | % yield | anti:syn | % ee |
|---|---|---|---|---|---|---|
| 1 | Me | Et | | 80 | 4:1 | 99 |
| 2 | Me | i-Bu | | 88 | 3:1 | 97 |
| 3 | Me | c-C$_6$H$_{11}$ | | 87 | 14:1 | 99 |
| 4 | Me | Ph | | 81 | 3:1 | 99 |
| 5 | Me | i-Pr | | 82 | 24:1 | >99 |
| 6 | n-Bu | i-Pr | | 80 | 24:1 | 98 |

TABLE 1-continued

| | | | 10 mol % L-Proline | | | |
|---|---|---|---|---|---|---|
| donor | | | DMF, + 4° C. | | | |

| entry | R[1] | R[2] | Product | % yield | anti:syn | % ee |
|---|---|---|---|---|---|---|
| 7 | Bn | i-Pr | (structure with O, OH, Me, Bn, Me) | 75 | 19:1 | 91 |

As demonstrated by the data in Table 1, addition of propionaldehyde, as an aldehyde donor, to a series of aldehyde acceptors in the presence of the amine catalyst provided excellent yields of the desired cross-aldol product. The data also demonstrate that propionaldehyde can be used as an aldol nucleophile with a broad range of aldehyde acceptors, including both alkyl- and aryl-substituted.

Entry 2, representing the addition of propionaldehyde to isovaleraldehyde, indicates that the reaction product was obtained in 88% yield and 97% ee. This indicates that the method of the invention is able to provide a single regioisomer despite the fact that both the aldol donor and accept bear enolizable α-methylene protons. Entries 5–7, corresponding to Examples 5–7, indicate that the aldol reaction can tolerate a range of structural variation in the aldehyde donor ($R^1$=Me, n-Bu, Bn, 19:1 to 24:1 anti:syn, 91 to >99% ee). In contrast to proline mediated ketone additions, lower catalyst loadings (10 mol %) and shorter reaction times (11 to 26 hours) were possible without loss in reaction efficiency (Hajos et al. (1974) Org. Chem. 39:1615; Eder et al. (1971) Angew. Chem. 10:496; Agami et al. (1987) Bull. Chim. Soc. Fr. 2:358). Entry 5 also illustrates the preparative utility of the reaction, insofar as the addition of propionaldehyde to isobutyraldehyde was performed on a 25 mmol scale to afford 2.65 g (82% yield) of (2S,3S)-3-hydroxy-2,4-dimethylpentanal in >99% ee with 24:1 anti-diastereoselectivity.

EXAMPLE 8

Synthesis of (2R, 3R, 4S, 5S, 6R)-6-ethyl-3,5-dimethyltetrahydro-2H-pyran-2,4-diol:

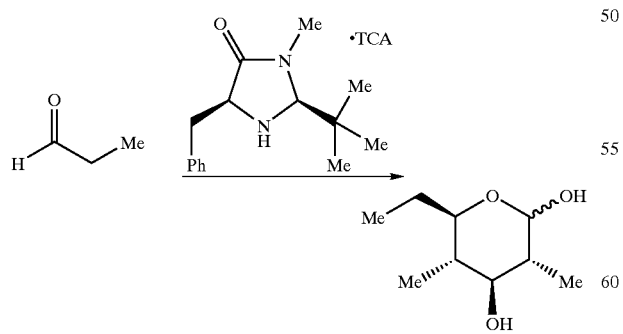

Propionaldehyde (108 μL, 1.5 mmol) was added to a solution of (2S,5S)-5-benzyl-2-tert-butyl-3-methylimidazolidin-4-one (24.6 mg, 0.10 mmol) and trichloroacetic acid (16.0 mg, 0.10 mmol) in 500 μL dioxane pre-cooled to +4° C. After stirring for 12 hours, a portion of the reaction mixture was withdrawn, diluted with $CH_2Cl_2$, washed with water, brine, dried over anhydrous $Na_2SO_4$, and concentrated to afford the title compound in 94% ee and 12:1 d.r. as a 1:1 mixture of anomers at C-2. IR (film) 3419, 2968, 2938, 2881, 2731, 1686, 1636, 1465, 1412, 1376, 1351, 1323, 1276, 1242, 1152, 1118, 1087, 1045, 1021, 1005, 972.4 cm$^{-1}$; $^1$H NMR (300 MHz, CDCl$_3$) δ5.16–4.93 (m, 1H, OCHOH); 4.56–4.49 (m, 1H, CH$_2$CH); 3.95, 3.60, 3.44, 3.14 (m, 1H, CHCHCHOH); 1.84–1.30 (m, 4H, CH$_2$, and 2 CHCH$_3$); 1.01–0.82 (m, 9H, 3 CH$_3$); $^{13}$C NMR (75 MHz, CDCl$_3$) δ101.0, 100.3, 99.8, 97.5, 96.7, 95.5, 94.8, 94.4, 81.8, 80.3, 77.5, 75.4, 41.7, 38.4, 36.9, 35.5, 28.1, 28.0, 25.9, 25.7, 25.4, 25.3, 12.5, 11.7, 10.7, 10.2, 10.1, 9.9, 9.6, 8.9, 8.7, 8.6, 4.3. Product ratios were determined by GLC analysis of the 2-acetoxy derivative (Ac$_2$O (3.0 equiv.), pyridine (10.0 equiv), in $CH_2Cl_2$ (1.0 M), r.t. 2.5 h) on an ASTEC Chiraldex γ-BP (30 m×0.25 mm) column. (90° C. isotherm, 23 psi); (2R, 3R, 4S, 5S, 6R) isomer t$_r$=38.3 min, (2S, 3R, 4S, 5S, 6R) isomer t$_r$=47.0 min, (2S, 3S, 4R, 5R, 6S) isomer t$_r$=39.4 min, (2R, 3S, 4R, 5R, 6S) isomer t$_r$=54.5 min, (2R, 3R, 4R, 5S, 6R) isomer t$_r$=49.9 min, (2S, 3R, 4R, 5S, 6R) isomer t$_r$=52.3 min, (2S, 3S, 4S, 5R, 6S) isomer t$_r$=40.5 min, (2R, 3S, 4S, 5R, 6S) isomer t$_r$=45.7 min.

EXAMPLE 9

Synthesis of 2,4-dimethyl-1-(4-nitro-phenyl)-pentane-1,3,5-triol:

The method of Example 4 was carried out substantially as described using the catalyst of Example 8, substituting 4-nitrobenzaldehyde for benzaldehyde and using two equivalents of propionaldehyde, giving 3,5-dihydroxy-2,4-dimethyl-5-(4-nitro-phenyl)-pentanal as the reaction product.

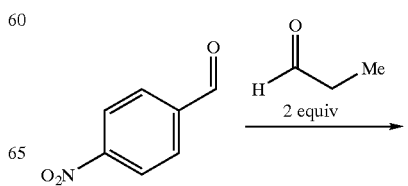

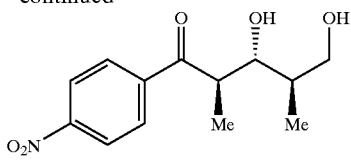

This dihydroxy aldehyde was then reduced with sodium borohydride to give the desired product

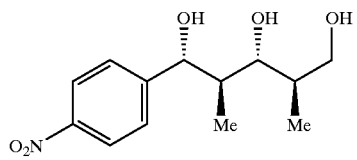

in 74% yield, 89% ee, and 13:1 (anti:syn:syn).

EXAMPLE 10

Synthesis of 2,4,6-tri-O-benzyl-D-glucopyranose:

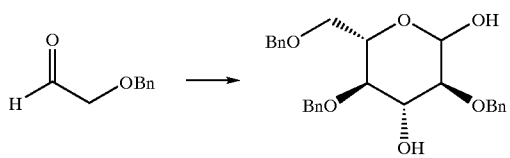

Freshly distilled benzyloxyacetaldehyde (150 mg, 1.0 mmol) was added to a stirring solution of (2S,5S)-5-benzyl-2-tert-butyl-3-methylimidazolidin-4-one trichloroacetate (27.3 mg, 67 μmol) in diethyl ether (330 μL, 3.0 M) at −20° C. After complete consumption of the starting material was determined by TLC analysis (24 h), the reaction mixture was diluted with ethyl acetate, washed with saturated NH$_4$Cl, brine, dried over anhydrous Na$_2$SO$_4$ and concentrated in vacuo. Flash chromatography (19:1 dichloromethane:diethyl ether) afforded the title compound as a clear, colorless oil in 85% yield (104 mg, 0.69 mmol), 95% ee, and 11:1 dr. $^1$H NMR (300 MHz, CDCl$_3$) δ7.31 (m, 15H, Ar—H), 5.38 (m, 1H, OCHO), 4.83 (m, 1H, CHCH$_2$), 4.55 (br, m, 5H), 4.12 (br m, 1H, 3.64 (br m, 4H, CHO), 3.30 (m, 1H, CHO); $^{13}$C NMR (75 MHz, CDCl$_3$) δ(α-anomer) 90.4 (C-1), 74.6 (C-3), and 68.9 (C-6); (β-anomer) 97.3 (C-1), 76.9 (C-3), 69.2 (C-6), which is consistent with previously reported values (Ito et al. (1980) *Carbohydrate Res.* 86:193).

EXAMPLE 11

Synthesis of 2,4-di-O-benzyl-6-acetoxy-D-glucopyranose: The method of Example 10 was repeated substantially as described using three equivalents of benzyloxyacetaldehyde and one equivalent of O-acetoxy acetaldehyde, to give the bis-differentially protected glucose molecule

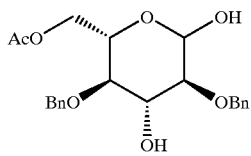

in 65% yield, 93% ee, and 6:1 (anti:syn:syn).

What is claimed is:

1. A method for carrying out an enantioselective aldol coupling reaction between aldehyde molecules, comprising contacting (a) an enolizable aldehyde and optionally (b) an additional aldehyde, with (c) a catalytically effective amount of a nonmetallic chiral catalyst containing a Group 15 or Group 16 heteroatom.

2. The method of claim 1, wherein the additional aldehyde is present, and the aldol coupling reaction is a cross-aldol reaction in which the α-carbon of the enolizable aldehyde undergoes nucleophilic addition to the carbonyl carbon of the additional aldehyde.

3. The method of claim 2, wherein the additional aldehyde is a non-enolizable aldehyde.

4. The method of claim 2, wherein the enolizable aldehyde has the structure of formula (I) and the additional aldehyde has the structure of formula (II)

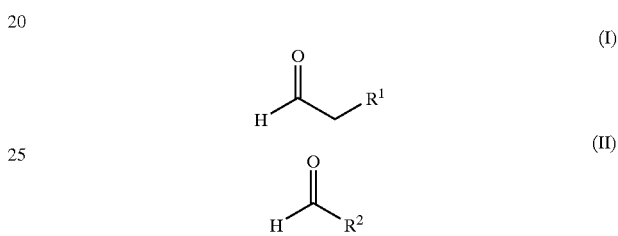

in which:

R$^1$ and R$^2$ are independently selected from hydrocarbyl, substituted hydrocarbyl, heteroatom-containing hydrocarbyl, and substituted heteroatom-containing hydrocarbyl.

5. The method of claim 4, wherein R$^1$ and R$^2$ are independently selected from C$_1$–C$_{24}$ alkyl, substituted C$_1$–C$_{24}$ alkyl, C$_1$–C$_{24}$ heteroalkyl, substituted C$_1$–C$_{24}$ heteroalkyl, C$_5$–C$_{24}$ aryl, substituted C$_5$–C$_{24}$ aryl, C$_1$–C$_{24}$ heteroaryl, substituted C$_1$–C$_{24}$ heteroaryl, C$_6$–C$_{24}$ aralkyl, substituted C$_6$–C$_{24}$ aralkyl, C$_1$–C$_{24}$ heteroaralkyl, and substituted C$_2$–C$_{24}$ heteroaralkyl.

6. The method of claim 5, wherein R$^1$ and R$^2$ are independently selected from C$_1$–C$_{12}$ alkyl, substituted C$_1$–C$_{12}$ alkyl, C$_1$–C$_{12}$ heteroalkyl, substituted C$_2$–C$_{12}$ heteroalkyl, C$_5$–C$_{14}$ aryl, substituted C$_5$–C$_{14}$ aryl, C$_3$–C$_{14}$ heteroaryl, substituted C$_3$–C$_{14}$ heteroaryl, C$_6$–C$_{16}$ aralkyl, substituted C$_6$–C$_{16}$ aralkyl, C$_3$–C$_{16}$ heteroaralkyl, and substituted C$_3$–C$_{16}$ heteroaralkyl.

7. The method of claim 2, wherein the catalyst is effective to raise the energy level of the highest occupied molecular orbital (HOMO) of the enolizable aldehyde.

8. The method of claim 2, wherein the heteroatom of the catalyst is selected from the group consisting of nitrogen, oxygen, sulfur and phosphorus.

9. The method of claim 8, wherein the heteroatom is nitrogen.

10. The method of claim 9, wherein the catalyst is a secondary amine or an acid addition salt thereof.

11. The method of claim 10, wherein the secondary amine is chiral with respect to an axis, plane or center of asymmetry.

12. The method of claim 11, wherein the secondary amine has the structure of (III)

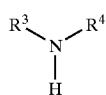

(III)

wherein R³ and R⁴ are independently selected from the group consisting of hydrocarbyl, substituted hydrocarbyl, heteroatom-containing hydrocarbyl, and substituted heteroatom-containing hydrocarbyl, or are taken together to form a ring, such that the amine is a cyclic secondary amine.

13. The method of claim 12, wherein R³ and R⁴ are taken together to form 3- to 15-membered, optionally substituted ring.

14. The method of claim 13, wherein the secondary amine has the structure of formula (IV)

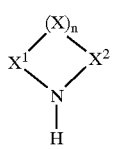

(IV)

wherein n is zero or 1, X is a moiety that contains up to 50 atoms and is selected from the group consisting of bydrocarbylene, substituted hydrocarbylene, heteroatom-containing hydrocarbylene and substituted heteroatom-containing hydrocarbylene, and X¹ and X² are independently substituted or unsubstituted methylene.

15. The method of claim 14, wherein the secondary amine has the structure of formula (V)

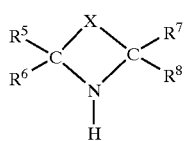

(V)

in which: $R^5$, $R^6$, $R^7$, and $R^8$ are independently selected from hydrogen, hydroxyl, sulfhydryl, carboxyl, amino, mono-($C_1$–$C_{24}$ alkyl-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, di-N-($C_1$–$C_{24}$ alkyl)-N-($C_5$–$C_{24}$ aryl)-substituted amino, $C_2$–$C_{24}$ alkylamido, $C_6$–$C_{24}$ arylamido, imino, $C_2$–$C_{24}$ alkylimino, $C_6$–$C_{24}$ arylimino, nitro, nitroso, $C_1$–$C_{24}$ alkoxy, $C_5$–$C_{24}$ aryloxy, $C_6$–$C_{24}$ aralkyloxy, $C_2$–$C_{24}$ alkylcarbonyl, ($C_6$–$C_{24}$ arylcarbonyl, $C_2$–$C_{24}$ alkylcarbonyloxy, $C_6$–$C_{24}$ arylcarbonyloxy, $C_2$–$C_{20}$ alkoxycarbonyl, $C_6$–$C_{24}$ aryloxycarbonyl, halocarbonyl, carbamoyl, mono-($C_1$–$C_{24}$ alkyl)-substituted carbamoyl, di-($C_1$–$C_{24}$ alkyl)-substituted carbamoyl, di-N-($C_1$–$C_{24}$ alkyl)-N-($C_5$–$C_{24}$ aryl)-substituted carbamoyl, mono-($C_5$–$C_{24}$ aryl)-substituted carbamoyl, di-($C_5$–$C_{24}$ aryl)-substituted carbamoyl, thiocarbamoyl, mono-($C_1$–$C_{24}$ alkyl)-substituted thiocarbamoyl, di-($C_1$–$C_{24}$ alkyl)-substituted thiocarbamoyl, di-N-($C_1$–$C_{24}$ alkyl)-N-($C_5$–$C_{24}$aryl)-substituted thiocarbamoyl, mono-($C_5$–$C_{24}$ aryl)-substituted thiocarbamoyl, di-($C_5$–$C_{24}$ aryl)-substituted thiocarbamoyl, carbamido, formyl, thioformyl, sulfo, sulfonato, $C_1$–$C_{24}$ alkylthio, $C_5$–$C_{24}$ arylthio, $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_2$–$C_{24}$ aralkyl, substituted $C_6$–$C_{24}$ aralkyl, $C_2$–$C_{24}$ heteroaralkyl, and substituted $C_2$–$C_{24}$ heteroaralkyl, or wherein $R^5$ and $R^6$ and/or $R^7$ and $R^8$, together form a carbonyl group =O.

16. The method of claim 15, wherein X is -($CR^9R^{10}$)-($X^3$)$_q$-($CR^{11}$–$R^{12}$)$_t$, and the secondary amine therefore has the structure of formula (VI)

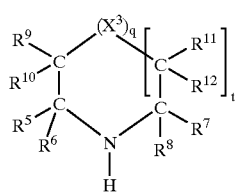

(VI)

in which $X^3$ is O, S, NH, $NR^{13}$, or $CR^{14}R^{15}$, q is zero or 1, t is zero or 1, and $R^9$, $R^{10}$, $R^{11}$, $R^{12}$, $R^{14}$, and $R^{15}$ are independently selected from hydrogen, hydroxyl, sulfhydryl, carboxyl, amino, mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, di-N-($C_1$–$C_{24}$ alkyl)-N-($C_5$–$C_{24}$ aryl)-substituted amino, $C_2$–$C_{24}$ alkylamido, $C_6$–$C_{24}$ arylamido, imino, $C_2$–$C_{24}$ alkylimino, $C_6$–$C_{24}$ arylimino, nitro, nitroso, $C_1$–$C_{24}$ alkoxy, $C_5$–$C_{24}$ aryloxy, $C_6$–$C_{24}$ aralkyloxy, $C_2$–$C_{24}$ alkylcarbonyl, $C_6$–$C_{24}$ arylcarbonyl, $C_2$–$C_{24}$ alkylcarbonyloxy, $C_6$–$C_{24}$ arylcarbonyloxy, $C_2$–$C_{20}$ alkoxycarbonyl, $C_6$–$C_{24}$ aryloxycarbonyl, halocarbonyl, carbamoyl, mono-($C_1$–$C_{24}$ alkyl)-substituted carbamoyl, di-($C_1$–$C_{24}$, alkyl)-substituted carbamoyl, di-N-($C_1$–$C_{24}$ alkyl)-N-($C_5$–$C_{24}$ aryl)-substituted carbamoyl, mono-($C_5$–$C_{24}$ aryl)-substituted carbamoyl, di-($C_5$–$C_{24}$ aryl)-substituted carbamoyl, thiocarbamoyl, mono-($C_1$–$C_{24}$ alkyl)-substituted thiocarbamoyl, di-($C_1$–$C_{24}$ alkyl)-substituted thiocarbamoyl, di-N-($C_1$–$C_{24}$ alkyl)-N-($C_5$–$C_{24}$ aryl)-substituted thiocarbamoyl, mono-($C_5$–$C_{24}$ aryl)-substituted thiocarbamoyl, di-($C_5$–$C_{24}$ aryl)-substituted thiocarbamoyl, carbamido, formyl, thioformyl, sulfo, sulfonato, $C_1$–$C_{24}$ alkylthio, $C_5$–$C_{24}$ arylthio, $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_2$–$C_{24}$ aralkyl, substituted $C_6$–$C_{24}$ aralkyl, $C_2$–$C_{24}$ heteroaralkyl, and substituted $C_2$–$C_{24}$ heteroaralkyl, or wherein $R^9$ and $R^{10}$, and/or $R^{11}$ and $R^{12}$, together form an oxo moiety =O; and $R^{13}$ is selected from $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl.

17. The method of claim 16, wherein q is zero, and at least one of $R^5$ through $R^8$ is carboxyl.

18. The method of claim 17, wherein the secondary amine is L-proline.

19. The method of claim 1, wherein the additional aldehyde is not present.

20. The method of claim 19, wherein the aldol coupling reaction comprises dimerization, trimerization, or polymerization of the enolizable aldehyde.

21. The method of claim 20, wherein the aldol coupling reaction comprises dimerization of the enolizable aldehyde.

22. The method of claim 20. wherein the aldol coupling reaction comprises trimerization of the enolizable aldehyde.

23. The method of claim 19, wherein the enolizable aldehyde has the structure of formula (I)

(I)

in which $R^1$ is selected from hydrocarbyl, substituted hydrocarbyl, heteroatom-containing hydrocarbyl, substituted heteroatom-containing hydrocarbyl, and functional groups.

24. The method of claim 23, wherein $R^1$ is selected from $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_6$–$C_{24}$ aralkyl, substituted $C_6$–$C_{24}$ aralkyl, $C_2$–$C_{24}$ heteroaralkyl, and substituted $C_2$–$C_{24}$ heteroaralkyl.

25. The method of claim 24, wherein $R^1$ is selected from $C_1$–$C_{12}$ alkyl, substituted $C_1$–$C_{12}$ alkyl, $C_1$–$C_{12}$ heteroalkyl, substituted $C_1$–$C_{12}$ heteroalkyl, $C_5$–$C_{14}$ aryl, substituted $C_5$–$C_{14}$ aryl, $C_3$–$C_{14}$ heteroaryl, substituted $C_3$–$C_{14}$ heteroaryl, $C_6$–$C_{16}$ aralkyl, substituted $C_6$–$C_{16}$ aralkyl, $C_3$–$C_{16}$ heteroaralkyl, and substituted $C_3$–$C_{16}$ heteroaralkyl.

26. The method of claim 19, wherein the catalyst is effective to raise the energy level of the highest occupied molecular orbital (HOMO) of the enolizable aldehyde.

27. The method of claim 19, wherein the heteroatom of the catalyst is selected from the group consisting of nitrogen, oxygen, sulfur and phosphorus.

28. The method of claim 27, wherein the heteroatom is nitrogen.

29. The method of claim 28, wherein the catalyst is a secondary amine or an acid addition salt thereof.

30. The method of claim 29, wherein the secondary amine is chiral with respect to an axis, plane or center of asymmetry.

31. The method of claim 30, wherein the secondary amine has the structure of (III)

(III)

wherein $R^3$ and $R^4$ are independently selected from the group consisting of hydrocarbyl, substituted hydrocarbyl, heteroatom-containing hydrocarbyl, and substituted heteroatom-containing hydrocarbyl, or are taken together to form a ring, such that the amine is a cyclic secondary amine.

32. The method of claim 31, wherein $R^3$ and $R^4$ are taken together to form a 3- to 15-membered, optionally substituted ring.

33. The method of claim 32, wherein the secondary amine has the structure of formula (IV)

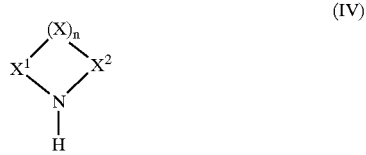

(IV)

wherein n is zero or 1, X is a moiety that contains up to 50 atoms and is selected from the group consisting of hydrocarbylene, substituted hydrocarbylene, heteroatom-containing hydrocarbylene and substituted heteroatom-containing hydrocarbylene, and $X^1$ and $X^2$ are independently substituted or unsubstituted methylene.

34. The method of claim 33, wherein the secondary amine has the structure of formula (V)

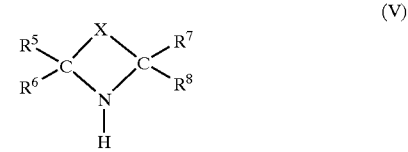

(V)

in which $R_5$, $R_6$, $R_7$, and $R_8$ are independently selected from hydrogen, hydroxyl, sulfhydryl, carboxyl, amino, mono-($C_1$–$C_{24}$ alkyl)-substituted amino, di-($C_1$–$C_{24}$ alkyl)-substitute amino, mono-($C_5$–$C_{24}$ aryl)-substituted amino, di-($C_5$–$C_{24}$ aryl)-substituted amino, di-N-($C_1$–$C_{24}$ alkyl)-N-($C_5$–$C_{24}$ aryl)-substituted amino, $C_2$–$C_{24}$ alkylamido, $C_6$–$C_{24}$ arylamido, imino, $C_2$–$C_{24}$ alkylimino, $C_6$–$C_{24}$ arylimino, nitro, nitroso, $C_1$–$C_{24}$ alkoxy, $C_5$–$C_{24}$ aryloxy, $C_6$–$C_{24}$ aralkyloxy, $C_2$–$C_{24}$ alkoxylcarbonyl, $C_6$–$C_{24}$ arylcarbonyl, $C_2$–$C_{24}$ alkylcarbonyloxy, $C_6$–$C_{24}$ arylcarbonyloxy, $C_2$–$C_{20}$ alkoxycarbonyl, $C_6$–$C_{24}$ aryloxycarbonyl, halocarbonyl, carbamoyl, mono-($C_1$–$C_{24}$ alkyl)-substituted carbamoyl, di-($C_1$–$C_{24}$ alkyl)-substituted carbamoyl, di-N-($C_1$–$C_{24}$ alkyl)-N-($C_5$–$C_{24}$ aryl)-substituted carbamoyl, mono-($C_5$–$C_{24}$ aryl)-substituted carbamoyl, di-($C_5$–$C_{24}$ aryl)-substituted carbamoyl, thiocarbamoyl, mono-($C_1$–$C_{24}$ alkyl)-substituted thiocarbamoyl, di-($C_1$–$C_{24}$ alkyl)-substituted thiocarbamoyl, di-N-($C_1$–$C_{24}$ alkyl)-N-($C_5$–$C_{24}$ aryl)-substituted thiocarbamoyl, mono-($C_5$–$C_{24}$ aryl)-substituted thiocarbamoyl, di-($C_5$–$C_{24}$ aryl)-substituted thiocarbamoyl, carbamido, formyl, thioformyl, sulfo, sulfonato, $C_1$–$C_{24}$ alkylthio, $C_5$–$C_{24}$ arylthio, $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_2$–$C_{24}$ aralkyl, substituted $C_6$–$C_{24}$ aralkyl, $C_2$–$C_{24}$ heteroaralkyl, and substituted $C_2$–$C_{24}$ heteroaralkyl, or wherein $R^5$ and $R^6$, and/or $R^7$ and $R^8$, together form an oxo moiety =O.

35. The method of claim 34, wherein X is -($CR^9R^{10}$)-($X^3$)$_q$-($CR^{11}R^{12}$)$_t$ and the secondary amine therefore has the structure of formula (VI)

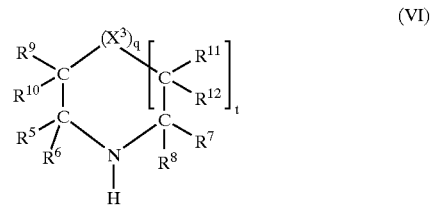

(VI)

wherein $X^3$ is O, S, NH, $NR^{13}$, or $CR^{14}R^{15}$, q is zero or 1, t is zero or 1, and $R^9$, $R^{10}$, $R^{11}$, $R^{12}$, $R^{14}$, and $R^{15}$ are independently selected from hydrogen, hydroxyl, sulfhydryl, carboxyl, amino, mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, di-N-($C_1$–$C_{24}$ alkyl)-N-($C_5$–$C_{24}$ aryl)-substituted amino, $C_2$–$C_{24}$ alkylamido, $C_6$–$C_{24}$ arylamido, imino, $C_2$–$C_{24}$ alkylimino, $C_6$–$C_{24}$ arylimino, nitro, nitroso, $C_1$–$C_{24}$ alkoxy, $C_5$–$C_{24}$ aryloxy, $C_6$–$C_{24}$ aralkyloxy, $C_2$–$C_{24}$ alkylcarbonyl, $C_6$–$C_{24}$ arylcarbonyl, $C_2$–$C_{24}$ alkylcarbonyloxy, $C_6$–$C_{24}$ arykarbonyloxy, $C_2$–$C_{20}$ alkoxycarbonyl, $C_6$–$C_{24}$ aryloxycarbonyl, halocarbonyl, carbamoyl, mono-($C_1$–$C_{24}$ alkyl)-substituted carbamoyl, di-($C_1$–$C_{24}$ alkyl)-substituted carbamoyl, di-N-($C_1$–$C_{24}$ alkyl)-N-($C_5$–$C_{24}$ aryl)-substituted carbamoyl, mono-($C_5$–$C_{24}$ aryl)-substituted carbamoyl, di-($C_5$–$C_{24}$ aryl)-substituted carbamoyl, thiocarbamoyl, mono-($C_1$–$C_{24}$ alkyl)-substituted thiocarbamoyl, di-($C_1$–$C_{24}$ alkyl)-substituted thiocarbamoyl, di-N-($C_1$–$C_{24}$ alkyl)-N-($C_5$–$C_{24}$ aryl)-substituted thiocarbamoyl, mono-($C_5$–$C_{24}$ aryl)-substituted thiocarbamoyl, di-($C_5$–$C_{24}$ aryl)-substituted thiocarbamoyl, carbamido, formyl, thioformyl, sulfo, sulfonato, $C_1$–$C_{24}$ alkylthio, $C_5$–$C_{24}$ arylthio, $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_2$–$C_{24}$ aralkyl, substituted $C_6$–$C_{24}$ aralkyl, $C_2$–$C_{24}$ heteroaralkyl, and substituted $C_2$–$C_{24}$ heteroaralkyl, or wherein $R^9$ and $R^{10}$, and/or $R^{11}$ and $R^{12}$, together form an oxo moiety =O; and $R^{13}$ is selected from $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl.

36. The method of claim 35, wherein q is zero, t is 1, and at least one of $R^5$ through $R_8$ is carboxyl.

37. The method of claim 36, wherein $R^5$ through $R^7$ and $R^9$ through $R^{12}$ are hydrogen, $R^8$ is carboxyl, and the secondary amine is L-proline.

38. The method of claim 35, wherein q is 1, $X^3$ is $NR^{13}$, t is zero, $R^5$ and $R^7$ are hydrogen, and $R^6$ is —$CR^{16}R^{17}R^{18}$, such that the secondary amine has the structure of formula (VIIA) or (VIB)

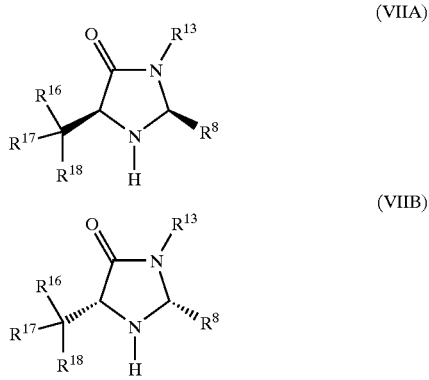

wherein:
$R_8$ and $R^{13}$ are as defined previously; and
$R^{16}$ and $R^{17}$ are independently selected from hydrogen, halo, hydroxyl, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl; and
$R^{18}$ is a cyclic group optionally substituted with 1 to 4 non-hydrogen substituents and containing zero to 3 heteroatoms.

39. The method of claim 38, wherein:
$R_8$ has the structure -(L)$_m$—$CR^{19}R^{20}R^{21}$ wherein m is zero or 1, L is $C_1$–$C_6$ alkylene, and $R^{19}$, $R^{20}$ and $R^{21}$ are $C_1$–$C_{12}$ hydrocarbyl;
$R^{13}$ is $C_1$–$C_{12}$ hydrocarbyl;
$R^{16}$ and $R^{17}$ are independently selected from hydrogen and $C_1$–$C_{12}$ hydrocarbyl; and
$R^{18}$ is a monocyclic aryl or heteroaryl group optionally substituted with 1 to 4 substituents selected from halo, hydroxyl, and $C_1$–$C_{12}$ hydrocarbyl.

40. The method of claim 39, wherein:
$R^{13}$ is $C_1$–$C_6$ alkyl;
$R^{16}$ and $R^{17}$ are hydrogen;
$R^{18}$ is phenyl optionally substituted with 1 or 2 substituents selected from halo, hydroxyl, and $C_1$–$C_6$ alkyl;
m is zero; and
$R^{19}$, $R^{20}$ and $R^{21}$ are $C_1$–$C_4$ alkyl.

41. The method of claim 40, wherein:
$R^{13}$, $R^{19}$, $R^{20}$ and $R^{21}$ are methyl; and
$R^5$ is phenyl.

42. The method of claim 29, wherein the catalyst is in the form of an acid addition salt composed of compound (VIIA) or (VIIB) and a Brønsted acid.

43. A composition comprising a nonmetallic chiral catalyst containing a Group 15 or Group 16 heteroatom, and an enolizable aldehyde having the structure of formula (I) and, optionally, an additional aldehyde has the structure of formula (II)

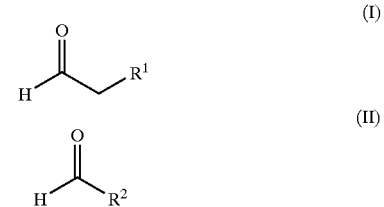

in which:
$R^1$ and $R^2$ are independently selected from hydrocarbyl, substituted hydrocarbyl, heteroatom-containing hydrocarbyl, and substituted heteroatom-containing hydrocarbyl.

44. The composition of claim 43, wherein the additional aldehyde is present.

45. The composition of claim 44, wherein $R^1$ and $R^2$ are independently selected from $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_6$–$C_{24}$ aralkyl, substituted $C_6$–$C_{24}$ aralkyl, $C_2$–$C_{24}$ heteroaralkyl, and substituted $C_2$–$C_{24}$ heteroaralkyl.

46. The composition of claim 45, wherein $R^1$ and $R^2$ are independently selected from $C_1$–$C_{12}$ alkyl, substituted $C_1$–$C_{12}$ alkyl, $C_1$–$C_{12}$ heteroalkyl, substituted $C_1$–$C_{12}$ heteroalkyl, $C_5$–$C_{14}$ aryl, substituted $C_5$–$C_{14}$ aryl, $C_3$–$C_{14}$ heteroaryl, substituted $C_3$–$C_{14}$ heteroaryl, $C_6$–$C_{16}$ aralkyl, substituted $C_6$–$C_{16}$ aralkyl, $C_3$–$C_{16}$ heteroaralkyl, and substituted $C_3$–$C_{16}$ heteroaralkyl.

47. The composition of claim 43, wherein the additional aldehyde is absent.

48. The composition of claim 47, wherein $R^1$ is selected from hydrogen, $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_6$–$C_{24}$ aralkyl.

49. The composition of claim 48, wherein $R^1$ is selected from hydrogen, $C_1$–$C_{12}$ alkyl, substituted $C_1$–$C_{12}$ alkyl, $C_1$–$C_{12}$ heteroalkyl, substituted $C_1$–$C_{12}$ heteroalkyl, $C_5$–$C_{14}$ aryl, substituted $C_5$–$C_{14}$ aryl, $C_3$–$C_{14}$ heteroaryl, substituted $C_3$–$C_{14}$ heteroaryl, $C_6$–$C_{16}$ aralkyl, substituted $C_6$–$C_{16}$ aralkyl, $C_3$–$C_{16}$ heteroaralkyl, and substituted $C_3$–$C_{16}$ heteroaralkyl.

50. The composition of claim 43, wherein the catalyst is effective to raise the energy level of the highest occupied molecular orbital (HOMO) of the enolizable aldehyde.

51. The composition of claim 43, wherein the heteroatom of the catalyst is selected from the group consisting of nitrogen, oxygen, sulfur and phosphorus.

52. The composition of claim 51, wherein the heteroatom is nitrogen.

53. The composition of claim 52, wherein the catalyst is a secondary amine or an acid addition salt thereof.

54. The composition of claim 53, wherein the secondary amine is chiral with respect to an axis, plane or center of asymmetry.

55. The composition of claim 54, wherein the secondary amine has the structure of (III)

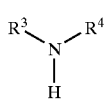

(III)

wherein $R^3$ and $R^4$ are independently selected from the group consisting of hydrocarbyl, substituted hydrocarbyl, heteroatom-containing hydrocarbyl, and substituted heteroatom-containing hydrocarbyl, or are taken together to form a ring, such that the amine is a cyclic secondary amine.

56. The composition of claim 55, wherein $R^3$ and $R^4$ are taken together to form a 3- to 15-membered, optionally substituted ring.

57. The composition of claim 56, wherein the secondary amine has the structure of formula (IV)

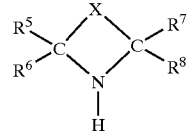

(IV)

wherein n is zero or 1, X is a moiety that contains up to 50 atoms and is selected from the group consisting of hydrocarbylene, substituted hydrocarbylene, heteroatom-containing hydrocarbylene and substituted heteroatom-containing hydrocarbylene, and $X^1$ and $X2$ are independently substituted or unsubstituted methylene.

58. The composition of claim 57, wherein the secondary amine has the structure of formula (V)

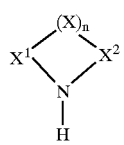

(V)

in which:

$R_5$, $R_6$, $R^7$, and $R^8$ are independently selected from hydrogen, hydroxyl, sulfhydryl carboxyl, amino, mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, di-N-($C_1$–$C_{24}$ alkyl)-N-($C_5$–$C_{24}$ aryl)-substituted amino, $C_2$–$C_{24}$ alkylamido, $C_6$–$C_{24}$ arylamido, imino, $C_2$–$C_{24}$ alkylimino, $C_6$–$C_{24}$ arylimino, nitro, nitroso, $C_1$–$C_{24}$ alkoxy, $C_5$–$C_{24}$ aryloxy, $C_6$–$C_{24}$ aralkyloxy, $C_2$–$C_{24}$ alkylcarbonyl, $C_6$–$C_{24}$ arylcarbonyl, $C_2$–$C_{24}$ alkylcarbonyloxy, $C_6$–$C_{24}$ aryloxycarbonyloxy, $C_2$–$C_{20}$ alkoxycarbonyl, $C_6$–$C_{24}$ aryloxycarbonyl, halocarbonyl, carbamoyl, mono-($C_1$–$C_{24}$ alkyl)-substituted carbamoyl, di-($C_1$–$C_{24}$ alkyl)-substituted carbamoyl, di-N-($C_1$–$C_{24}$ alkyl)-N-($C_5$–$C_{24}$ aryl)-substituted carbamoyl, mono-($C_5$–$C_{24}$ aryl)-substituted carbamoyl, di-($C_5$–$C_{24}$ aryl)-substituted carbamoyl, thiocarbamoyl, mono-($C_1$–$C_{24}$ alkyl)-substituted thiocarbamoyl, di-($C_1$–$C_{24}$ alkyl)-substituted thiocarbamoyl, di-N-($C_1$–$C_{24}$ alkyl)-N-($C_5$–$C_{24}$ aryl)-substituted thiocarbamoyl, mono-($C_5$–$C_{24}$ aryl)-substituted thiocarbamoyl, di-($C_5$–$C_{24}$ aryl)-substituted thiocarbamoyl, carbamido, formyl, thioformyl, sulfo, sulfonato, $C_1$–$C_{24}$ alkylthio, $C_5$–$C_{24}$ arylthio, $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ heteroaryl, $C_2$–$C_{24}$ aralkyl, substituted $C_6$–$C_{24}$ aralkyl, $C_2$–$C_{24}$ heteroaralkyl, and substituted $C_2$–$C_{24}$ heteroaralkyl, or wherein $R^5$ and $R_6$, and/or $R^7$ and $R_8$, together form a carbonyl group =O.

59. The composition of claim 58, wherein X is -($CR^9R^{10}$)- ($X^3$)$_q$-($CR^{11}R^{12}$)$_t$, and the secondary amine therefore has the structure of formula (VI)

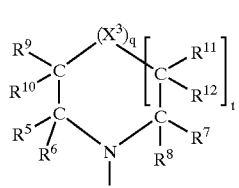

(VI)

in which $X^3$ is O, S, NH, $NR^{13}$, or $CR^{14}R^{15}$, q is zero or 1, t is zero or 1, and $R^9$, $R^{10}$, $R^{11}$, $R^{12}$, $R^{14}$, and $R^{15}$ are independently selected from hydrogen, hydroxyl, sulfhydryl, carboxyl, amino, mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, di-N-($C_1$–$C_{24}$ alkyl)-N-($C_5$–$C_{24}$ aryl)-substituted amino, $C_2$–$C_{24}$ alkylamido, $C_6$–$C_{24}$ arylamido, imino, $C_2$–$C_{24}$ alkylimino, $C_6$–$C_{24}$ arylimino, nitro, nitroso, $C_1$–$C_{24}$ alkoxy, $C_5$–$C_{24}$ aryloxy, $C_6$–$C_{24}$ aralkyloxy, $C_2$–$C_{24}$ alkylcarbonyl, $C_6$–$C_{24}$ arylcarbonyl, $C_2$–$C_{24}$ alkylcarbonyloxy, $C_6$–$C_{24}$ arylcarbonyloxy, $C_2$–$C_{20}$ alkoxycarbonyl, $C_6$–$C_{24}$ aryloxycarbonyl, halocarbonyl, carbamoyl, mono-($C_1$–$C_{24}$ alkyl)-substituted carbamoyl, di-($C_1$–$C_{24}$ alkyl)-substituted carbamoyl, di-N-($C_1$–$C_{24}$ alkyl)-N-($C_5$–$C_{24}$ aryl)-substituted carbamoyl, mono-($C_5$–$C_{24}$ aryl)-substituted carbamoyl, di-($C_5$–$C_{24}$ aryl)-substituted carbamoyl, thiocarbamoyl, mono-($C_1$–$C_{24}$ alkyl)-substituted thiocarbainoyl, di-($C_1$–$C_{24}$ alkyl)-substituted thiocarbamoyl, di-N-($C_1$–$C_{24}$ alkyl)-N-($C_5$–$C_{24}$ aryl)-substituted thiocarbamoyl, mono-($C_5$–$C_{24}$ aryl)-substituted thiocarbamoyl, di-($C_5$–$C_{24}$ aryl)-substituted thiocarbamoyl, carbamido, formyl, thioformyl, sulfo, sulfonato, $C_1$–$C_{24}$ alkylthio, $C_5$–$C_{24}$ arylthio, $C_1$–$C_{24}$ alkyl, substituted $C_1$–$C_{24}$ alkyl, $C_1$–$C_{24}$ heteroalkyl, substituted $C_1$–$C_{24}$ heteroalkyl, $C_5$–$C_{24}$ aryl, substituted $C_5$–$C_{24}$ aryl, $C_1$–$C_{24}$ heteroaryl, substituted $C_1$–$C_{24}$ beteroaryl, $C_2$–$C_{24}$ aralkyl, substituted $C_6$–$C_{24}$ aralkyl, $C_2$–$C_{24}$ heteroaralkyl, and substituted $C_2$–$C_{24}$ heteroaralkyl, or wherein $R^9$ and $R^{10}$, and/or $R^{11}$ and $R^{12}$, together form an oxo moiety =O; and $R^{13}$ is selected from $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_1$, hydrocarbyl.

60. The composition of claim 59, wherein q is zero, and at least one of $R^5$ through $R^8$ is carboxyl.

61. The composition of claim 60, wherein the secondary amine is L-proline.

62. The composition of claim 61, wherein q is 1, $X^3$ is $NR^{13}$, is zero, $R^5$ and $R^7$ are hydrogen, and $R^6$ is —$CR^{16}R^{17}R^{18}$, such that the secondary amine has the structure of formula (VIIA) or (VIIB)

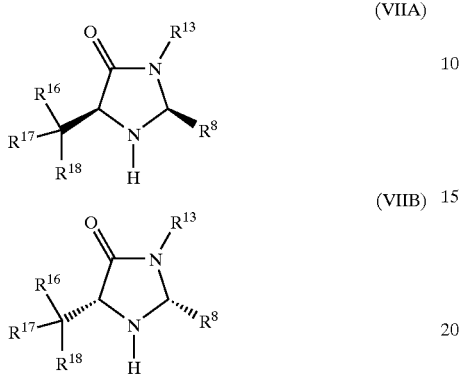

wherein:

$R_8$ and $R^{13}$ are as defined previously; and $R^{16}$ and $R^{17}$ are independently selected from hydrogen, halo, hydroxyl, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl; and $R^{18}$ is a cyclic group optionally substituted with 1 to 4 non-hydrogen substituents and containing zero to 3 heteroatoms.

63. The composition of claim 62, wherein:

$R_8$ has the structure -$(L)_m$—$CR^{19}R^{20}R^{21}$ wherein in is zero or 1, L is $C_1$–$C_6$ alkylene, and $R^{19}$, $R^{20}$ and $R^{21}$ are $C_1$–$C_{12}$ hydrocarbyl;

$R^{13}$ is $C_1$–$C_{12}$ hydrocarbyl;

$R^{16}$ and $R^{17}$ are independently selected from hydrogen and $C_1$–$C_{12}$ hydrocarbyl; and $R^{18}$ is a monocyclic aryl or heteroaryl group optionally substituted with 1 to 4 substituents selected from halo, hydroxyl, and $C_1$–$C_{12}$ hydrocarbyl.

64. The composition of claim 63, wherein:

$R^{13}$ is $C_1$–$C_6$ alkyl;

$R^{16}$ and $R^{17}$ are hydrogen;

$R^{18}$ is phenyl optionally substituted with 1 or 2 substituents selected from halo, hydroxyl, and $C_1$–$C_6$ alkyl;

m is zero; and $R^{19}$, $R^{20}$ and $R^{21}$ are $C_1$–$C_4$ alkyl.

65. The composition of claim 64, wherein:

$R^{13}$, $R^{19}$ $R^{20}$ and $R^{21}$ are methyl; and $R^5$ is phenyl.

66. The composition of claim 65, wherein the catalyst is in the form of an acid addition salt composed of compound (VIIA) or (VIIB) and a Brønsted acid.

* * * * *